US010550163B2

(12) United States Patent
Cai et al.

(10) Patent No.: US 10,550,163 B2
(45) Date of Patent: Feb. 4, 2020

(54) PEPTIDE FRAGMENTS OF NETRIN-1 AND COMPOSITIONS AND METHODS THEREOF

(71) Applicant: The Regents of the University of California, Oakland, CA (US)

(72) Inventors: Hua Cai, Los Angeles, CA (US); Qiang Li, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/300,071

(22) PCT Filed: Mar. 30, 2015

(86) PCT No.: PCT/US2015/023248
§ 371 (c)(1),
(2) Date: Sep. 28, 2016

(87) PCT Pub. No.: WO2015/153402
PCT Pub. Date: Oct. 8, 2015

(65) Prior Publication Data

US 2017/0210780 A1 Jul. 27, 2017

Related U.S. Application Data

(60) Provisional application No. 61/974,710, filed on Apr. 3, 2014.

(51) Int. Cl.

| | |
|---|---|
| ***A61K 38/04*** | (2006.01) |
| ***A61K 38/08*** | (2019.01) |
| ***A61K 38/10*** | (2006.01) |
| ***C07K 7/00*** | (2006.01) |
| ***C07K 7/06*** | (2006.01) |
| ***C07K 7/08*** | (2006.01) |
| ***C07K 14/435*** | (2006.01) |
| *A61K 38/00* | (2006.01) |

(52) U.S. Cl.
CPC ............ *C07K 14/435* (2013.01); *A61K 38/00* (2013.01)

(58) Field of Classification Search
None
See application file for complete search history.

(56) References Cited

U.S. PATENT DOCUMENTS 5,665,862 A 9/1997 Fishbach et al.
8,168,593 B2 5/2012 Plouet et al.
2004/0034196 A1 2/2004 Komatsoulis et al.
2010/0183588 A1 7/2010 Plouet et al.
2011/0280876 A1 11/2011 Plouet et al.
2016/0184396 A1 6/2016 Song et al.

FOREIGN PATENT DOCUMENTS

WO 2014190860 A1 12/2014

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Li and Cai. (2015). Am J Physiol Cell Physiol. 309(2):C100-C106.*
Extended European Search Report received in EP 15773612, dated Oct. 25, 2017.
Accession No. UPI000029C45E, Jul. 19, 2005, Publisher: UniProt Database.
International Search Report received in PCT/US2015/023248, dated Jul. 31, 2015.
Shannon, et al., "A hypomorphic mutation in the mouse laminin alpha5 gene causes polycystic kidney disease", Jun. 21, 2006, pp. 1913-1922, vol. 17, No. 7, Publisher: J Am Soc Nephrol.
Written Opinion received in PCT/US2015/023248, dated Jul. 31, 2015.
Bouhidel, et al., "Netrin-1 improves post-injury cardiac function in vivo via DCC/NO-dependent preservation of mitochondrial integrity, while attenuating autophagy", Jun. 10, 2014, pp. 277-289, vol. 1852, Publisher: Biochimica et Biophysica Acta.
Siu, et al., "Netrin-1 abrogates ischemia/reperfusion-induced cardiac mitochondrial dysfunction via nitric oxide-dependent attenuation of NOX4 activation . . . ", Jul. 24, 2014, pp. 174-185, vol. 78, Publisher: Journal of Molecular and Cellular Cardiology.

* cited by examiner

*Primary Examiner* — Daniel E Kolker
*Assistant Examiner* — Jon M Lockard
(74) *Attorney, Agent, or Firm* — Suzannah K. Sundby, Esq.; Canady + Lortz LLP

(57) ABSTRACT

Disclosed herein are peptide fragments derived from netrin-1 and compositions thereof and methods of using thereof. In some embodiments, the present invention provides a peptide that is 8-65 amino acid residues long and has a core sequence having Formula I as follows: CX(1-2)CX(3-4)TX(0-1)G, wherein X is any amino acid residue. In some embodiments, the present invention provides a composition comprising one or more peptides of the present invention which have a core sequence according to Formula I, Formula IA, or Formula IB.

CX(1-2)CX(3-4)TX(0-1)g (I)

17 Claims, 11 Drawing Sheets

Specification includes a Sequence Listing.

PEPTIDE FRAGMENTS OF NETRIN-1 AND COMPOSITIONS AND METHODS THEREOF

ACKNOWLEDGEMENT OF GOVERNMENT SUPPORT

This invention was made with Government support under Grant Number HL119968, awarded by the National Institutes of Health. The Government has certain rights in the invention.

REFERENCE TO A SEQUENCE LISTING SUBMITTED VIA EFS-WEB

The content of the ASCII text file of the sequence listing named "20171004_034044_144WO1_subseq_ST25" which is 6.62 kb in size was created on Oct. 4, 2017, and electronically submitted via EFS-Web Oct. 4, 2017 is incorporated herein by reference in its entirety.

BACKGROUND OF THE INVENTION

1. Field of the Invention

The present invention relates to peptide fragments derived from netrin-1, compositions thereof, and methods of treatment employing the peptide fragments.

2. Description of the Related Art

Netrins and their receptors are well known in the art, as exemplified in U.S. Pat. Nos. 5,565,331; 6,096,866; 6,017,714; 6,309,638; 6,670,451; and 8,168,593; and in US20060019896 and US20060025335.

Netrin-1 is a secreted molecule that is largely known to play a defined role in guiding vertebrate commissural axons in neuronal development. See Kennedy et al. (1994) Cell 78:425-35; Serafini et al. (1994) Cell 78:409-24; and Serafini et al. (1996) Cell 87:1001-14. Recent studies have further demonstrated a critical role of netrin-1 in endothelial cell proliferation, migration, and angiogenic signaling, in addition to morphogenesis of epithelial cells. See Park et al. (2004) PNAS USA 101:16210-5; Lu et al. (2004) Nature 432:179-86; Carmeliet et al. (2005) Nature 436:193-200; Nguyen et al. (2006) PNAS USA 103:6530-5; Wilson et al. (2006) Science 313:640-4; Navankasattusas et al. (2008) Development 135:659-67; Liu et al. (2004) Curr Biol 14:897-905; and Nikolopoulos et al. (2005) Cell Cycle 4:e131-5. At least eight netrin receptors have been characterized in neurons, vascular system, and other cell types in mammals. These include deleted in colorectal cancer (DCC), UNCSA, B, C, D, neogenin, α6β4, and α3β1 integrins. See Tessier-Lavigne et al. (1996) Science 274:1123-33; Huber et al. (2003) Annu Rev Neurosci 26:509-63; Cirulli et al. (2007) Nat Rev Mol Cell Biol 8:296-306; and Yebra et al. (2003) Dev Cell 5:695-707. Netrin-1 binding to DCC mediates attractive outgrowth of axons, as well as positive angiogenic signalings in endothelial and vascular smooth muscle cells. In contrast, the UNC5B receptor appears repulsive, mediating cellular effects such as filopodial retraction, particularly in developing capillaries. See Lu et al. (2004) Nature 432:179-86; and Larrivee et al. (2007) Genes Dev 21:2433-47.

SUMMARY OF THE INVENTION

In some embodiments, the present invention provides a peptide that is 8-65 amino acid residues long and has a core sequence having Formula I as follows: $CX_{(1-2)}CX_{(3-4)}TX_{(0-1)}G$ (SEQ ID NO: 10) (I) wherein X is any amino acid residue. In some embodiments, the core sequence is represented by Formula IA as follows: C-X1-X2-C-X3-X4-X5-X6-T-X7-G (SEQ ID NO: 11) (IA) wherein X1 may be present or absent, and if present, X1 is selected from the group consisting of A, V, L, I, P, F, M, and W, and analogs and isomers thereof, preferably X1 is L or P; X2 may be present or absent, and if present, X2 is selected from the group consisting of D, E, G, N, Q, S, T, Y, and C, and analogs and isomers thereof, preferably X2 is D or N; X3 is selected from the group consisting of K, R, and H and analogs and isomers thereof, preferably X3 is R or K; X4 is selected from the group consisting of D, E, K, R, H, Y, F, and W, and analogs and isomers thereof, preferably X4 is D or H; X5 is selected from the group consisting of G, N, Q, S, T, Y, and C, and analogs and isomers thereof, preferably X5 is N or G; X6 may be present or absent and if present, X6 is selected from the group consisting of T, V, and I, and analogs and isomers thereof, preferably X6 is V; and X7 may be present or absent, and if present, X7 is selected from the group consisting of A, V, L, I, P, F, M, and W, and analogs and isomers thereof, preferably X7 is A; and wherein either X1, X2, or both X1 and X2 are present. In some embodiments, the core sequence is represented by Formula IB as follows: C-X1-X2-C-R-H-N-T-A-G (SEQ ID NO: 12) (IB) wherein X1 may be present or absent, and if present, X1 is selected from the group consisting of A, V, L, I, P, F, M, and W, and analogs and isomers thereof, preferably X1 is L or P; and X2 may be present or absent, and if present, X2 is selected from the group consisting of D, E, G, N, Q, S, T, Y, and C, and analogs and isomers thereof, preferably X2 is D or N; and wherein either X1, X2, or both X1 and X2 are present. In some embodiments, the peptide is about 8-60, about 8-55, about 8-50, about 8-35, about 8-30, about 8-20, about 8-15, about 8-12, 8-11, about 9-60, about 9-55, about 9-50, about 9-35, about 9-30, about 9-20, about 9-15, about 9-12, or 9-11 amino acid residues long. In some embodiments, the peptide is 8, 9, 10, or 11 amino acid residues long. In some embodiments, the peptide is about 12-47 amino acid residues long. In some embodiments, at least one amino acid residue is different from the corresponding amino acid residue of a netrin-1 sequences found in nature, e.g., human netrin-1. In some embodiments, the peptide has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments, the peptide has been chemically and/or physically modified to improve or increase its biological half-life, stability, efficacy, bioavailability, bioactivity, or a combination thereof, as compared to its unmodified form. In some embodiments, the peptide comprises, consists essentially of, or consists of the core sequence. In some embodiments, the peptide is isolated, purified, or both.

In some embodiments, the present invention provides a composition comprising one or more peptides of the present invention which have a core sequence according to Formula I, Formula IA, or Formula IB. In some embodiments, the peptide is about 8-60, about 8-55, about 8-50, about 8-35, about 8-30, about 8-20, about 8-15, about 8-12, 8-11, about 9-60, about 9-55, about 9-50, about 9-35, about 9-30, about 9-20, about 9-15, about 9-12, or 9-11 amino acid residues long. In some embodiments, the peptide is 8, 9, 10, or 11 amino acid residues long. In some embodiments, the peptide is 12-47 amino acid residues long. In some embodiments, at least one amino acid residue is different from the corresponding amino acid residue of a netrin-1 sequence found in nature, e.g., human netrin-1. In some embodiments, the peptide has an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments, the peptide comprises, consists essentially of, or consists of the core sequence. In some embodiments, the peptide is isolated, purified, or both. In some embodiments, the composition comprises a concentrated or purified amount of one or more peptides, wherein the concentration and/or purification level is one that is not found in nature. In some embodiments, the amount of the one or more peptides provided in the composition is a therapeutically effective amount. In some embodiments, the peptide has been chemically and/or physically modified to improve or increase its biological half-life, stability, efficacy, bioavailability, bioactivity, or a combination thereof, as compared to its unmodified form. In some embodiments, the composition comprises a first peptide containing a core sequence according to Formula IA wherein X1 is absent, and a second peptide containing a core sequence according to Formula IA wherein X1 and X2 are present. In some embodiments, the first peptide and the second peptide are present in synergistic amounts. In some embodiments, the composition is prepared and/or formulated to improve or increase the biological half-life, stability, efficacy, bioavailability, bioactivity, or a combination thereof, of the one or more peptides as compared to their unmodified form. In some embodiments, the composition comprises, consists essentially of, or consists of the one or more peptide fragments.

The present invention also provides various methods using the one or more peptides or compositions as disclosed herein. In some embodiments, the present invention provides a method of stimulating, increasing, or enhancing nitric oxide production by endothelial cells, which comprises administering to the endothelial cells one or more peptides having Formula I, Formula IA, or Formula IB, or a composition thereof. In some embodiments, the present invention provides a method of stimulating or inducing phosphorylation of ERK1/2 and/or eNOS in endothelial cells, which comprises administering to the endothelial cells one or more peptides having Formula I, Formula IA, or Formula IB, or a composition thereof. In some embodiments, the present invention provides a method of treating, inhibiting, or reducing an injury to a tissue or organ having endothelial cells which comprises stimulating, increasing, or enhancing nitric oxide production by the endothelial cells and/or stimulating or inducing phosphorylation of ERK1/2, eNOS, or both in the endothelial cells by administering to the endothelial cells, before, during, and/or after the injury, one or more peptides having Formula I, Formula IA, or Formula IB, or a composition thereof. In some embodiments, the endothelial cells are vascular endothelial cells. In some methods according to the present invention, the administration to the endothelial cells is in vivo administration. In some embodiments, the injury is caused by superoxide production, ischemia/reperfusion, or myocardial infarction. In some embodiments, the tissue is cardiac tissue. In some embodiments, the organ is a heart. In some embodiments, the injury is caused by myocardial infarction and the administration reduces the infarct size of the heart. In some embodiments, the present invention provides a method of treating, inhibiting, or reducing an ischemia/reperfusion injury to an organ, e.g., a heart, in a subject, comprising administering a therapeutically effective amount of one or more peptides having Formula I, Formula IA, or Formula IB, or a composition thereof to the subject, thereby treating, inhibiting or reducing the ischemia/reperfusion injury. In some embodiments, the present invention provides a method of decreasing or reducing the infarct size of a heart in a subject resulting from an ischemialreperfusion injury, comprising administering a therapeutically effective amount of one or more peptides having Formula I, Formula IA, or Formula IB, or a composition thereof to the subject, thereby decreasing or reducing the infarct size. In some embodiments, the subject is a mammalian subject. In some embodiments, the subject is an animal model, e.g., a mouse. In some embodiments, the subject is a human. In some embodiments, the subject being treated with one or more peptide fragments or compositions according to the present invention is one who is in need thereof. Subjects who are in need thereof include those who may benefit from stimulating, increasing, or enhancing nitric oxide production, those who may benefit from stimulating or inducing phosphorylation of ERK1/2 and/or eNOS, those who have or may have a tissue or organ injury resulting from superoxide production, ischemia/reperfusion, or myocardial infarction, and those who will be or will likely be exposed to increased superoxide production, ischemia/reperfusion conditions, or myocardial infarction.

In some embodiments, the present invention provides a human-made package, e.g., a kit, comprising therein one or more peptides having Formula I, Formula IA, or Formula IB, or a composition thereof. In some embodiments, the human-made package further includes a drug delivery device.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1A are representative Western blots and grouped densitometric data of ERK1/2 phosphorylation (Mean±SEM, n=5).

FIG. 1B are representative Western blots and grouped densitometric data of $eNOS_{s1179}$ phosphorylation (Mean±SEM, n=4). *p<0.001, p<0.01, *p<0.05 vs. 0 minutes.

FIG. 1C schematically shows the structural composition of Netrin-1, including: a Laminin VI like domain, three repeats of Laminin V like domains (V1, V2, V3), and a C-terminal C345C domain.

FIG. 2A are representative Western blots and grouped densitometric data of ERK1/2 phosphorylation induced by peptide fragment V1 (Mean±SEM, n=5).

FIG. 2B are representative Western blots and grouped densitometric data of $eNOS_{s1179}$ phosphorylation induced by peptide fragment V1 (Mean±SEM, n=5).

FIG. 2C are representative Western blots and grouped densitometric data of ERK1/2 phosphorylation induced by peptide fragment V2 (Mean±SEM, n=6).

FIG. 2D are representative Western blots and grouped densitometric data of $eNOS_{s1179}$ phosphorylation induced by peptide fragment V2 (Mean±SEM, n=6).

FIG. 2E are representative Western blots and grouped densitometric data of ERK1/2 phosphorylation induced by peptide fragment V3 (Mean±SEM, n=6).

FIG. 2F are representative Western blots and grouped densitometric data of $eNOS_{s1179}$ phosphorylation induced by peptide fragment V3 (Mean±SEM, n=6). *p<0.001, p<0.01, *p<0.05 vs. 0 minutes.

FIG. 3A schematically shows the experimental procedure. Hearts of C57BL6 mice were freshly isolated and subjected to ischemia reperfusion (I/R) injury using a Langendorff perfusion system. Hearts were pre-perfused with Krebs-Henseleit buffer for 30 minutes, followed by a 45 minute perfusion with netrin-1 peptide fragment V1, V2, or V3 at the same molar concentration of 1.47 nmol/L. Then I/R injury was consistently produced by subjecting the hearts to 20 minutes of normo-thermic ischemia, followed by reperfusion for 60 minutes with or without corresponding peptides. Sections of the hearts were stained with 2,3,5-TTC and infarct area calculated as % of risk area.

FIG. 3B are representative TTC stains (inverse color shown) of I/R-injured mouse hearts.

FIG. 3C is a graph providing the quantitative grouped data of the experiments performed according to FIG. 3A, Control I/R (n=4), I/R w. V1 (n=5), I/R w. V2 (n=4), I/R w. V3 (n=3), Mean±SEM, ***p<0.001 vs. control I/R. The control was without the addition of any peptides and taken at time 0.

FIG. 4A schematically shows the experimental procedure. Hearts of C57BL6 mice were freshly isolated and subject to ischemia reperfusion (I/R) injury using a Langendorff perfusion system. Hearts were pre-perfused with Krebs-Henseleit buffer for 40 minutes, and then I/R injury was consistently produced by subjecting the hearts to 20 minutes of normo-thermic ischemia, followed by reperfusion for 60 minutes with or without peptide fragment V1, V2, or V3 at the same molar concentration of 1.47 nmol/L. Sections of hearts were stained with 2,3,5-TTC and infarct area calculated as % of risk area.

FIG. 4B are representative TTC stains (inverse color shown) of I/R-injured mouse hearts.

FIG. 4C is a graph providing the quantitative grouped data of the experiments performed according to FIG. 4A, Control I/R (n=5), I/R w. V1 (n=5), I/R w. V2 (n=3), I/R w. V3 (n=5), Mean±SEM, ***p<0.001 vs. control I/R. The control was without the addition of any peptides and taken at time 0.

FIG. 5A is a representative TTC stain (inverse color shown) of I/R-injured mouse hearts.

FIG. 5B is a graph providing the quantitative grouped data of experiments performed, Control I/R (n=5), I/R w. V1-9aa (n=3), I/R w. V2-10aa (n=3), I/R w. V3-16aa (n=4), I/R w. V3-11aa (n=4), Mean±SEM, ***p<0.001 vs. control I/R. The control was without the addition of any peptides and taken at time 0.

FIG. 5C shows the alignment of three short netrin-1 peptide fragments which reveals the minimal core sequences that result in cardioprotection. The sequence identifiers of the three sequences from top to bottom are: SEQ ID NO: 4, SEQ ID NO: 5, and SEQ ID NO: 6.

FIG. 6A is a representative ESR spectra.

FIG. 6B is a graph providing the quantitative grouped data. n=5-6, Mean±SEM, ***p<0.001 vs. control.

FIG. 7A is a representative ESR spectra.

FIG. 7B is a graph providing the quantitative grouped data. n=5-14, Mean±SEM, *p<0.001, p<0.01, *p<0.05 vs. Control. # p<0.05 vs. V1-9aa group.

DETAILED DESCRIPTION OF THE INVENTION

Figure 1A:
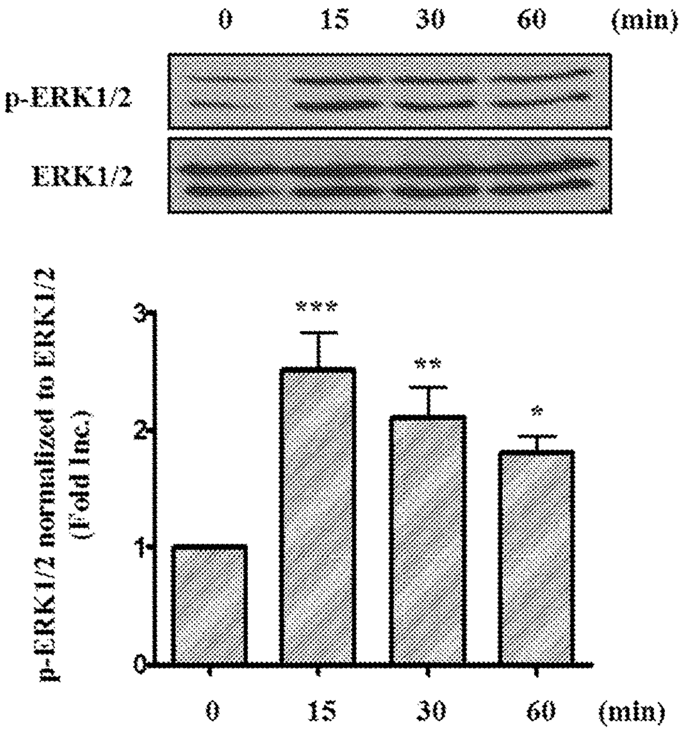
FIGS. 1A-1C show that Netrin-1 induces phosphorylation of ERK1/2 and $eNOS_{s1179}$: Bovine aortic endothelial cells were stimulated by netrin-1 (100 ng/ml, molar concentration 1.47 nmol/L) and harvested at different time points (0, 15, 30, 60 minutes). Western blots were performed to detect phosphorylated ERK1/2, ERK1/2, phosphorylated eNOS at Ser1179, and eNOS levels.

The present invention provides novel fragments derived from netrin-1 which exhibit cardioprotective activity when administered to subjects. It is important to note that the peptide fragments according to the present invention are not simply "isolates" of the full-length netrin-1 protein as peptide fragments of the present invention exhibit levels of cardioprotection which are significantly more than that achieved with the full-length netrin-1. Specifically, as disclosed herein, the peptide fragments according to the present invention result in an infarct size that is less than 20%. Thus, the peptide fragments according to the present invention are markedly different from netrin-1 as found in nature.

As disclosed herein, short peptide fragments based on the full-length netrin-1 protein were designed and assayed for their efficacies in inducing cardioprotection against ischemia reperfusion (I/R) injuries. As used herein, the terms "protein", "polypeptide", "peptide", and "peptide fragments" are used interchangeably to refer to two or more natural and/or unnatural amino acids linked together and one letter amino acid designations are used in the sequences and formulas herein. As used herein, "aa" is an abbreviation used for "amino acids". For example, the "9aa" of "V1-9aa" indicates that the peptide is 9 amino acid residues long.

When delivered to the heart, the peptide fragments of the present invention activate the protective pathway turned on by netrin-1, namely DCC-dependent activation of ERK1/2 and eNOS. ERK1/2, and $eNOS_{s1177}$ (1177 residue for human/mouse while 1179 for bovine) phosphorylation were time-dependently increased by the peptide fragments in cultured endothelial cells, which is believed to increase nitric oxide (NO) production to exert cardioprotection. Indeed, analysis of post-I/R infarct size indicated significant reduction in myocardial injury after treatment with peptide fragments according to the present invention. These data have clearly indicated potent cardioprotective efficacies of netrin-1 derived peptide fragments, including V1, V2, and V3 peptide fragments, and shorter peptide fragments containing a core sequence having Formula I.

As disclosed herein, it was found that peptide fragments comprising a core sequence having Formula I activate the protective pathway turned on by netrin-1, namely DCC-dependent activation of ERK1/2 and eNOS. The core sequence having Formula I (SEQ ID NO: 10) is as follows:

$$CX_{(1-2)}CX_{(3-4)}TX_{(0-1)}G \qquad (I)$$

wherein X is any amino acid residue.

In some embodiments, the core sequence is represented by Formula IA (SEQ ID NO: 11) as follows:

C-X1-X2-C-X3-X4-X5-X6-T-X7-G (IA)

wherein

X1 may be present or absent, and if present, X1 is selected from the group consisting of A, V, L, I, P, F, M, and W, and analogs and isomers thereof, preferably X1 is L or P;

X2 may be present or absent, and if present, X2 is selected from the group consisting of D, E, G, N, Q, S, T, Y, and C, and analogs and isomers thereof, preferably X2 is D or N;

X3 is selected from the group consisting of K, R, and H and analogs and isomers thereof, preferably X3 is R or K;

X4 is selected from the group consisting of D, E, K, R, H, Y, F, and W, and analogs and isomers thereof, preferably X4 is D or H;

X5 is selected from the group consisting of G, N, Q, S, T, Y, and C, and analogs and isomers thereof, preferably X5 is N or G;

X6 may be present or absent and if present, X6 is selected from the group consisting of T, V, and I, and analogs and isomers thereof, preferably X6 is V; and X7 may be present or absent, and if present, X7 is selected from the group consisting of A, V, L, I, P, F, M, and W, and analogs and isomers thereof, preferably X7 is A; and wherein either X1, X2, or both X1 and X2 are present.

In some embodiments, the core sequence is represented by Formula IB (SEQ ID NO: 12) as follows:

C-X1-X2-C-R-H-N-T-A-G (IB)

wherein

X1 may be present or absent, and if present, X1 is selected from the group consisting of A, V, L, I, P, F, M, and W, and analogs and isomers thereof, preferably X1 is L or P; and X2 may be present or absent, and if present, X2 is selected from the group consisting of D, E, G, N, Q, S, T, Y, and C, and analogs and isomers thereof, preferably X2 is D or N; and wherein either X1, X2, or both X1 and X2 are present.

In some embodiments, the peptide fragments of the present invention, which comprise a core sequence according to Formula I, Formula IA, or Formula IB, are about 8-60, about 8-55, about 8-50, about 8-35, about 8-30, about 8-20, about 8-15, about 8-12, 8-11, about 9-60, about 9-55, about 9-50, about 9-35, about 9-30, about 9-20, about 9-15, about 9-12, or 9-11 amino acid residues long. In some embodiments, the peptide fragments of the present invention, which comprise a core sequence according to Formula I, Formula IA, or Formula IB, are about 8-60, about 8-55, about 8-50, about 8-35, about 8-30, about 8-20, about 8-15, about 8-12, 8-11, about 9-60, about 9-55, about 9-50, about 9-35, about 9-30, about 9-20, about 9-15, about 9-12, or 9-11 amino acid residues long and have at least one amino acid residue or from one amino acid residue up to about 1% of its amino acid residues that are different from the corresponding amino acid residues of netrin-1 sequences found in nature, e.g., human netrin-1. In some embodiments, the peptide fragments of the present invention, which comprise a core sequence according to Formula I, Formula IA, or Formula IB, are about 8-60, about 8-55, about 8-50, about 8-35, about 8-30, about 8-20, about 8-15, about 8-12, 8-11, about 9-60, about 9-55, about 9-50, about 9-35, about 9-30, about 9-20, about 9-15, about 9-12, or 9-11 amino acid residues long and have at least one amino acid residue up to about 10 amino acid residues that are different from the corresponding amino acid residues of netrin-1 sequences found in nature, e.g., human netrin-1. In some embodiments, the peptide fragments of the present invention, which comprise a core sequence according to Formula I, Formula IA, or Formula IB, are about 8-60, about 8-55, about 8-50, about 8-35, about 8-30, about 8-20, about 8-15, about 8-12, 8-11, about 9-60, about 9-55, about 9-50, about 9-35, about 9-30, about 9-20, about 9-15, about 9-12, or 9-11 amino acid residues long and have, in the core sequence, at least one amino acid residue up to about 7 amino acid residues that are different from the corresponding amino acid residues of netrin-1 sequences found in nature, e.g., human netrin-1. In some embodiments, the peptide fragments comprising a core sequence according to Formula I, Formula IA, or Formula IB are 8, 9, 10, or 11 amino acid residues long. In some embodiments, the peptide fragments comprising a core sequence according to Formula I, Formula IA, or Formula IB are 12-47 amino acid residues long. In some embodiments, the peptide fragments comprising a core sequence according to Formula I, Formula IA, or Formula IB are shorter than V1, V2, and/or V3.

In some embodiments, peptide fragments according to the present invention comprise, consist essentially of, or consist of a core sequence according to Formula I, Formula IA, or Formula IB. As used herein, a peptide fragment that "comprises" a core sequence according to Formula I, Formula IA, or Formula IB means that the peptide fragment may include additional amino acid residues, amino acid isomers, and/or amino acid analogs at the N-terminus, the C-terminus, or both. The additional residues may or may not change the activity or function of the core sequence, e.g., increase or decrease the activity of the peptide as compared to the activity of the core sequence itself. As used herein, a peptide fragment that "consists essentially of" a core sequence according to Formula I, Formula IA, or Formula IB means that the peptide fragment may include additional amino acid residues, amino acid isomers, and/or amino acid analogs at the N-terminus, the C-terminus, or both, so long as the additional residues do not materially change the function or activity of the core sequence. As used herein, a peptide fragment that "consists of" a core sequence according to Formula I, Formula IA, or Formula IB means that the peptide fragment does not include additional amino acid residues, amino acid isomers, and/or amino acid analogs at both the N-terminus and the C-terminus.

In some embodiments, the peptide fragments of the present invention may be isolated. As used herein, an "isolated" compound refers to a compound which is isolated from its native environment. For example, an isolated peptide is one which does not have its native amino acids, which correspond to the full length polypeptide, flanking the N-terminus, C-terminus, or both. For example, an isolated V1-9aa peptide refers to a peptide having amino acid residues (304-312 aa) of V1, which may have non-native amino acids at its N-terminus, C-terminus, or both, but does not have a proline amino acid residue following its 9th amino acid residue at the C-terminus, or a valine amino acid residue immediately preceding the cysteine amino acid residue at its N-terminus, or both. As another example, an isolated peptide can be one which is immobilized to a substrate with which the peptide is not naturally associated. As a further example, an isolated peptide can be one which is linked to another molecule, e.g. a PEG compound, with which the peptide is not naturally associated.

In some embodiments, peptide fragments according to the present invention may comprise one or more natural amino acids, unnatural amino acids, or a combination thereof. The amino acid residues of the peptide fragments may be D-isomers, L-isomers, or both. The peptide fragments may be composed of α-amino acids, β-amino acids, natural amino acids, non-natural amino acids, amino acid analogs, or a combination thereof. Amino acid analogs include β-amino acids and amino acids where the amino or carboxy group is substituted by a similarly reactive group (e.g., substitution of the primary amine with a secondary or tertiary amine, or substitution of the carboxy group with an ester).

Examples of β-amino acid analogs include cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl) butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethyl-phenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Examples of amino acid analogs of alanine, valine, glycine, and leucine include α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl) glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene) ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Examples of amino acid analogs of arginine and lysine include citrulline; L-2-amino-3-guanidinopropionic acid; L-2-amino-3-ureidopropionic acid; L-citrulline; Lys(Me)2-OH; Lys(N3)-OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nγ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene) ethyl)-L-ornithine; (Nδ-4-methyltrityl)-D-ornithine; (Nδ-4-methyltrityl)-L-ornithine; D-ornithine; L-ornithine; Arg (Me)(Pbf)-OH; Arg(Me)2-OH (asymmetrical); Arg(Me)2-OH (symmetrical); Lys(ivDde)-OH; Lys(Me)2-OH.HCl; Lys(Me3)-OH chloride; Nω-nitro-D-arginine; and Nω-nitro-L-arginine.

Examples of amino acid analogs of aspartic and glutamic acids include α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OA11)-OH; L-Asu(OtBu)-OH; and pyroglutamic acid.

Examples of amino acid analogs of cysteine and methionine include Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichlorophenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Examples of amino acid analogs of proline include 3,4-dehydro-proline, 4-fluoro-proline, cis-4-hydroxy-proline, thiazolidine-2-carboxylic acid, and trans-4-fluoro-proline.

Examples of amino acid analogs of serine and threonine include 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Examples of amino acid analogs of tryptophan include α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, peptide fragments of the present invention may comprise one or more non-essential amino acids. A non-essential amino acid residue can be a residue that can be altered from the wild-type sequence of a polypeptide without abolishing or substantially altering its essential biological or biochemical activity (e.g., receptor binding or activation).

In some embodiments, peptide fragments of the present invention may comprise one or more conservative amino acid substitutions. A conservative amino acid substitution is one in which the amino acid residue is replaced with an amino acid residue having a side chain. Amino acids with basic side chains include K, R, and H, amino acids with acidic side chains include D and E, amino acids with uncharged polar side chains include G, N, Q, S, T, Y, and C, amino acids with nonpolar side chains include A, V, L, I, P, F, M, and W, amino acids with beta-branched side chains include T, V, and I, and amino acids with aromatic side chains include Y, F, W, and H.

The peptide fragments of the present invention are advantageous over the full-length netrin-1 protein because they are shorter in size, and as a result, may be 1) conveniently and successfully produced in large quantities, 2) more affordable, and 3) activate the protective pathway with less or reduced side effects as compared to the full-length netrin-1.

Therefore, in some embodiments, one or more peptide fragments according to the present invention may be used to treat acute myocardial infarction in subjects. In some embodiments, one or more peptide fragments according to the present invention may be used to treat, inhibit, or reduce ischemia/reperfusion injury to cardiac tissue in a subject. As used herein, the term "ischemia/reperfusion injury" (I/R injury) refers to an injury of an organ, e.g., heart, caused by putting the organ into an ischemic condition such as by thomboembolic events, surgery, or cardiac standstill. Clinically relevant situations include occlusion of coronary arteries/branches that happen during myocardial infarction (ischemia). Treatment with percutaneous transluminal coronary angioplasty (PTCA) procedure creates a reperfusion condition that is known to cause additional injury that can be however protected by pharmacological post-conditioning (administering peptide fragments according to the present invention at the reperfusion stage). Therefore, in some embodiments, the present invention is also directed towards acute treatment of myocardial infarction by administering one or more peptide fragments according to the present invention (e.g., intravenously) alone or in combination with PTCA/drug eluting stent. In some embodiments, the peptide fragments of the present invention may be used to reduce or inhibit the infarct size of cardiac tissue and/or treat, inhibit, or reduce damage to cardiac tissue resulting from myocardial infarction.

Additionally, as disclosed herein, the peptide fragments of the present invention can induce phosphorylation of ERK1/2, $eNOS_{s1177}$, and/or $eNOS_{s1179}$. Therefore, in some embodiments, one or more peptide fragments of the present invention are used to induce phosphorylation of ERK1/2, $eNOS_{s1177}$, and/or $eNOS_{s1179}$ in subjects.

Also, as disclosed herein, the peptide fragments of the present invention can induce nitric oxide production. Therefore, in some embodiments, one or more peptide fragments of the present invention are used to increase nitric oxide production in subjects.

The following examples are intended to illustrate but not to limit the invention.

Netrin-1 Induces Phosphorylation of ERK1/2 and $eNOS_{s1179}$

Figure 1B:
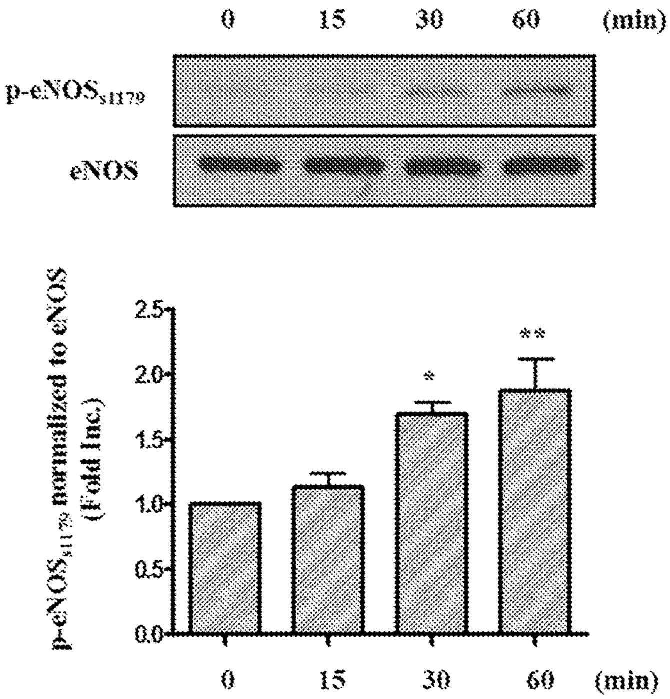

Netrin-1 functions as a potent angiogenic stimulator via a DCC-dependent ERK1/2-eNOS feed-forward mechanism. In addition, netrin-1 as a robust cardioprotective agent, which attenuates ischemia/reperfusion induced myocardial infarction via a similar DCC/ERK1/2/$eNOS_{s1177/}$NO signaling pathway. In order to identify the minimal functional domain, which could simulate netrin-1 to activate its receptor DCC to activate downstream signaling events such as eNOS phosphorylation, the effect of netrin-1 on phosphorylation of ERK1/2 and $eNOS_{s1179}$ in endothelial cells was examined at different time points. As showed in FIG. 1A, exposure of bovine aortic endothelial cells (BAECs) to netrin-1 (100 ng/ml) resulted in a consistent increase in ERK1/2 phosphorylation, which maximized at 15 minutes (2.52±0.31 fold vs. 0 minutes, $p<0.001$). As shown in FIG. 1B, $eNOS_{s1179}$ phosphorylation was time-dependent upregulated by netrin-1, maximizing at 30 minutes (1.70±0.09 fold vs. 0 minutes, $p<0.05$) and 60 minutes (1.88±0.25 fold vs. 0 minutes, $p<0.01$). Thus, netrin-1 can induce ERK1/2 and $eNOS_{s1179}$ phosphorylation, the pathway important for netrin-1 mediated cardioprotection.

Figure 1C:
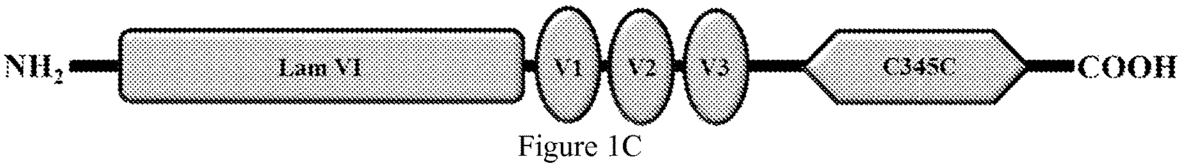
Figure 2A:
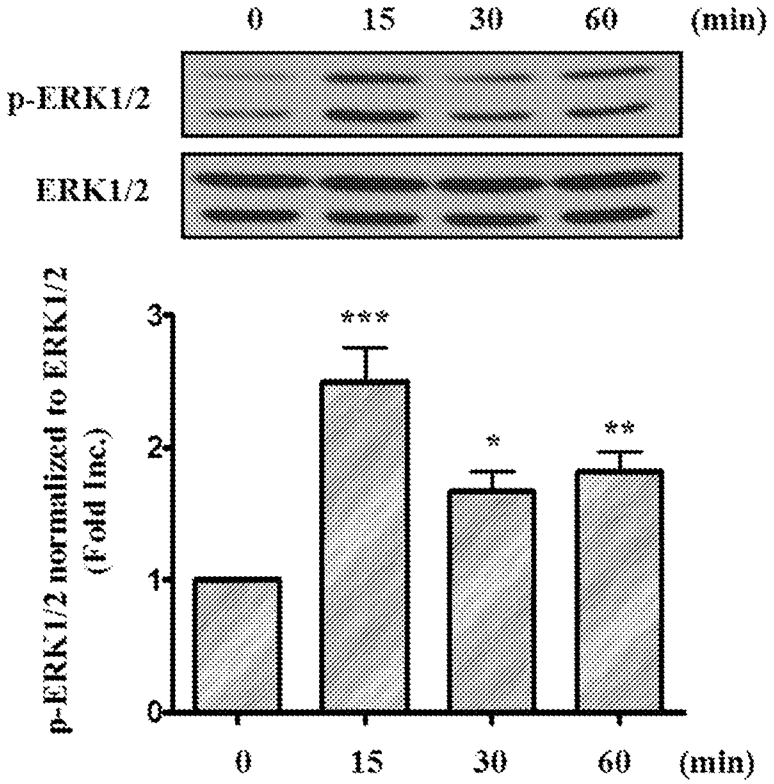
FIGS. 2A-2F show that Netrin-1 peptide fragments V1, V2, and V3 induce phosphorylation of ERK1/2 and $eNOS_{s1179}$: Bovine aortic endothelial cells were stimulated by netrin-1 peptide fragment V1, V2, or V3 at the same molar concentration of 1.47 nmol/L, and harvested at different time points (0, 15, 30, 60 minutes). Western blots were performed to detect phosphorylated ERK1/2, ERK1/2, phosphorylated eNOS at Ser1179, and eNOS levels.
Figure 2B:
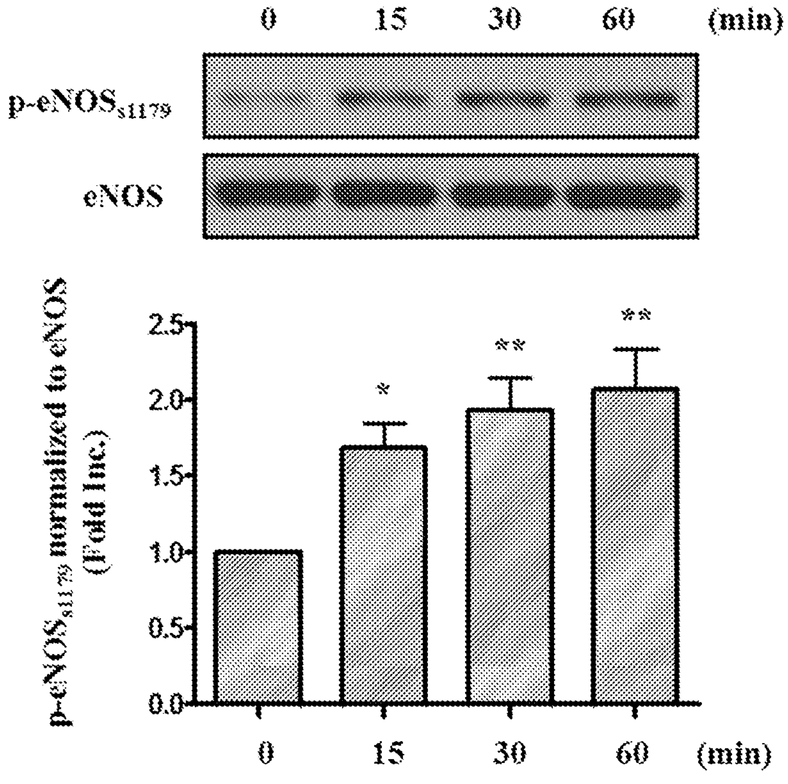
Figure 2C:
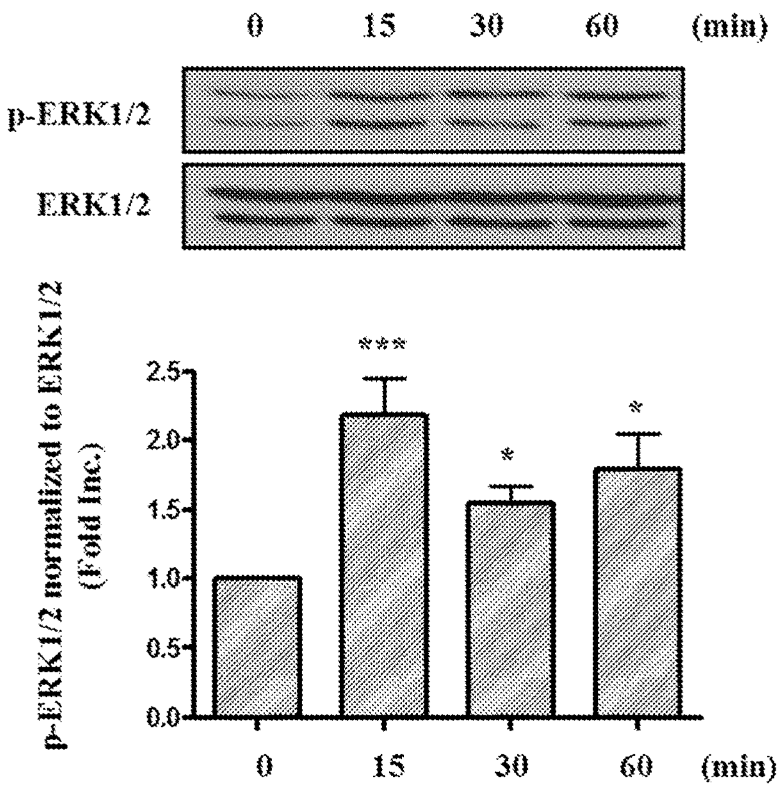
Figure 2D:
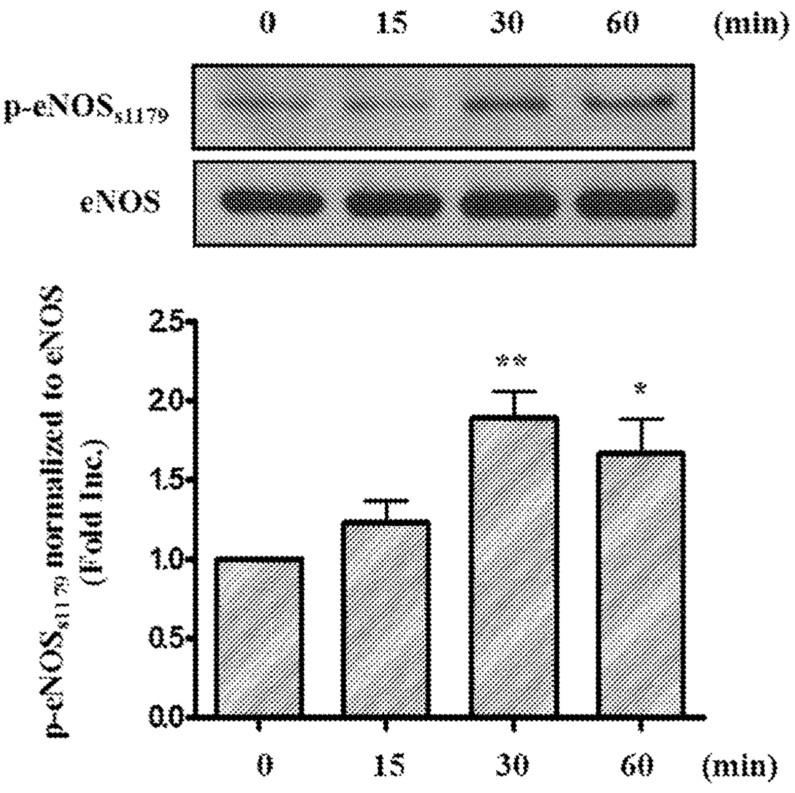
Figure 2E:
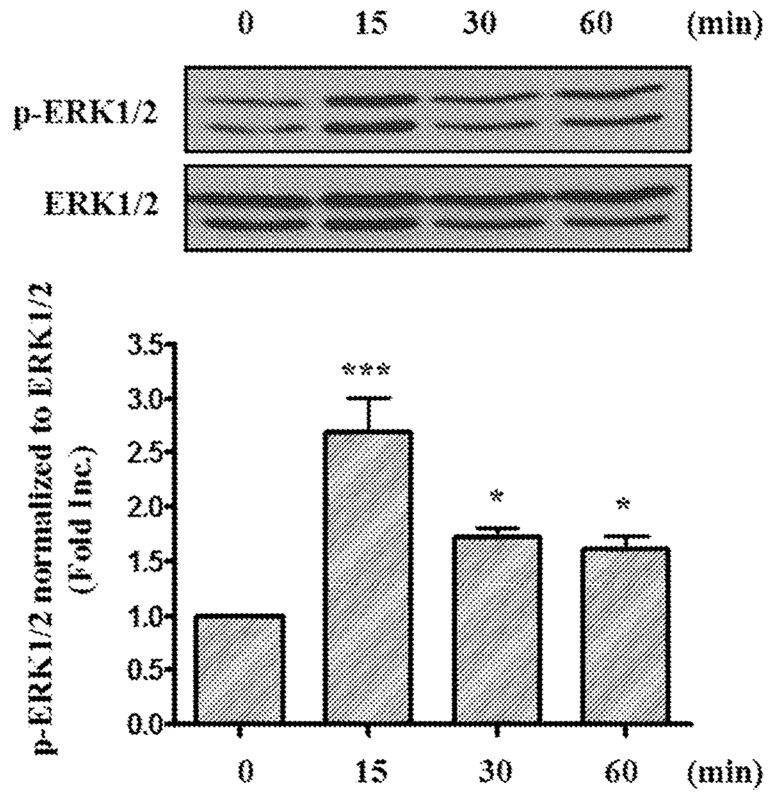
Figure 2F:
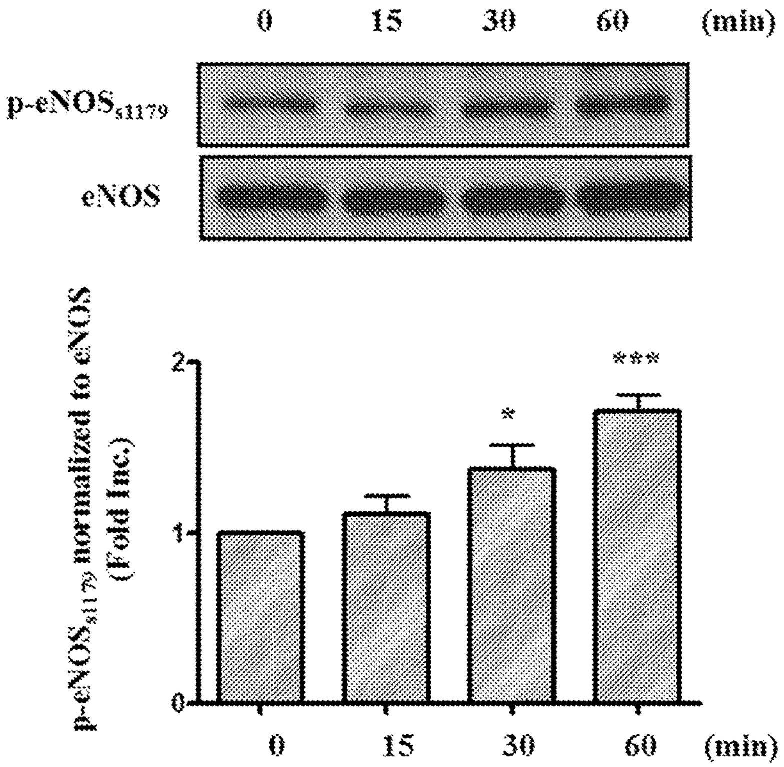

Peptide Fragments V1, V2, and V3 Induce Phosphorylation of ERK1/2 and $eNOS_{s1179}$ As shown in FIG. 1C, netrin-1 has a Laminin VI like (named Lam VI) domain, three cysteine-rich repeats similar to those of domain V of Laminin subunits (named Lam V, including V1, V2, and V3), and a C-terminal domain (named C345C) with homology to complement factors C3, C4, and C5. The Lam VI domain and Lam V domain are involved in the association with its receptor DCC. Lam VI, V2, and V3 domains are believed to be required primarily for the dorsal axon guidance activities of netrin-1 homolog UNC-6 in *Caenorhabditis elegans*. Therefore, these three domains have the potential to simulate netrin-1's biological function in the cardiovascular system. Peptide fragments V1 (residues 285-338), V2 (residues 341-401) and V3 (residues 404-451), were synthesized and used to treat bovine aortic endothelial cells (BAECs) at the same molar concentration (1.47 nmol/L) as used for netrin-1 (100 ng/ml). As shown in FIG. 2, of note, the V1, V2, and V3 peptide fragments activate the phosphorylation of ERK1/2 in endothelial cells, and the response maximized at 15 minutes (V1: 2.47±0.27 fold vs. 0 minutes, $p<0.001$; V2: 2.18±0.27 fold vs. 0 minutes, $p<0.001$; V3: 2.69±0.31 fold vs. 0 minutes, $p<0.001$), which were similar to the response to netrin-1 (FIG. 2A, 2C, 2E). Furthermore, these peptide fragments also significantly induced phosphorylation of $eNOS_{s1179}$ at 30 minutes (V1: 1.93±0.22 fold vs. 0 minutes, $p<0.01$; V2: 1.89±0.16 fold vs. 0 minutes, $p<0.01$; V3: 1.37±0.14 fold vs. 0 minutes, $p<0.05$) and 60 minutes (V1: 2.07±0.24 fold vs. 0 minutes, $p<0.01$; V2: 1.67±0.22 fold vs. 0 minutes, $p<0.05$; V3: 1.72±0.10 fold vs. 0 minutes, $p<0.001$) (FIG.

2B, 2D, 2F). Taken together, these data strongly suggest that the V1, V2, and V3 peptide fragments activate the netrin-1 responsive, downstream signaling pathway involved in cardioprotection.

Therefore, in some embodiments, the present invention is directed to activating phosphorylation of ERK1/2 and/or eNOS in a subject by administering a therapeutically effective amount of one or more V1, V2, or V3 peptide fragments to the subject. In some embodiments, the present invention is directed to protecting cardiac tissue from injury or reducing or inhibiting injury to cardiac tissue in a subject which comprises activating phosphorylation of ERK1/2 and/or eNOS in a subject by administering a therapeutically effective amount of one or more V1, V2, or V3 peptide fragments to the subject.

Figure 3A:
FIGS. 3A-3C show that Netrin-1 peptide fragments V1, V2, and V3 induce potent cardioprotection against ischemia/reperfusion injury.
Figure 3B:
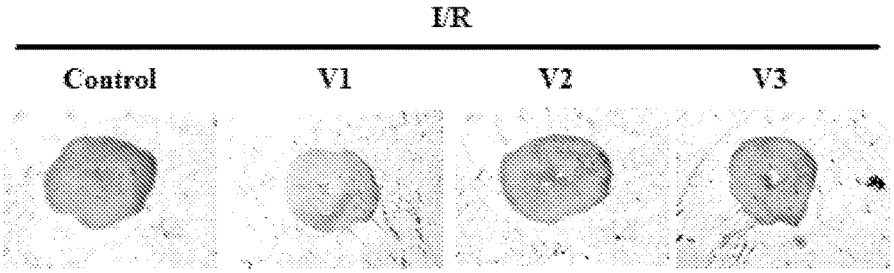
Figure 3C:
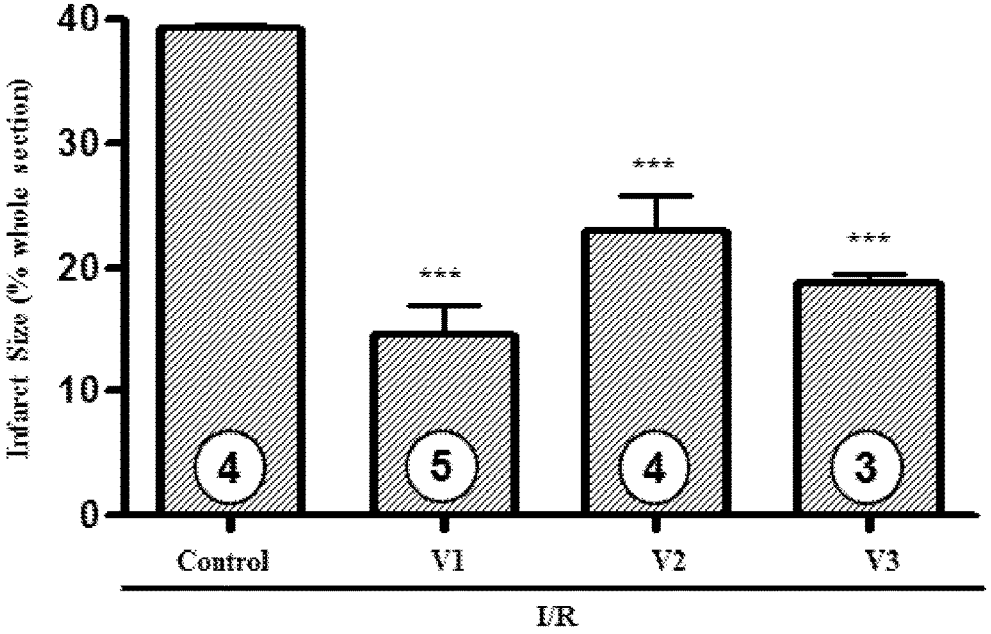
Figure 4A:
FIGS. 4A-4C show that Netrin-1 peptide fragments V1, V2, and V3 induce potent cardioprotection against ischemia/reperfusion injury post-conditioningly.
Figure 4B:
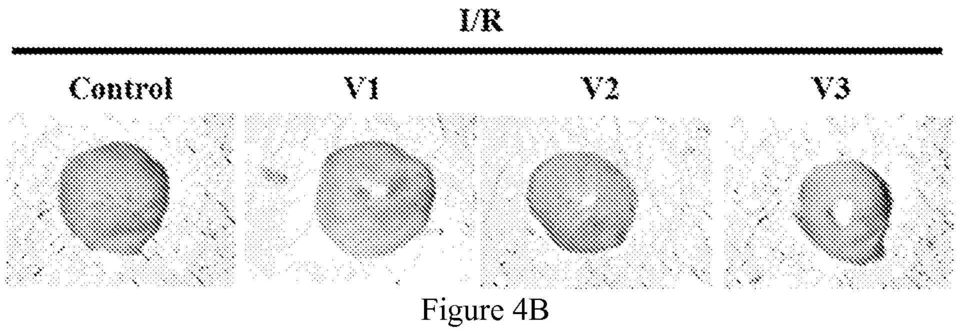
Figure 4C:
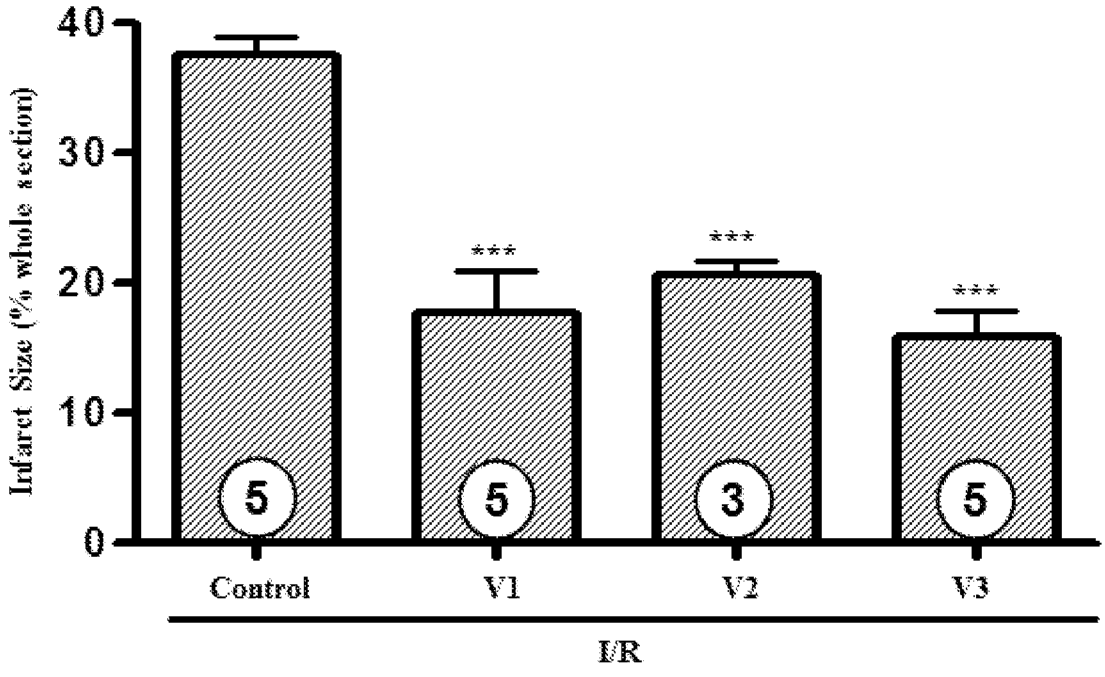

Peptide Fragments V1, V2, and V3 Induce Cardioprotection Against Ischemia/Reperfusion Injury Since netrin-1 is cardioprotective via DCC/ERK1/2/$eNOS_{s1177}$/NO signaling in the heart, and peptide fragments V1, V2, and V3 also activate phosphorylation of ERK1/2 and $eNOS_{s1179}$, whether these peptide fragments can induce similar cardioprotection was examined. When administered before an ischemia/reperfusion injury, V1, V2, or V3 perfused hearts had a substantial reduction in infarct size (Control I/R: 39.3±0.3% vs. I/R w. V1: 14.6±2.3% vs. I/R w. V2: 23.0±2.8% vs. I/R w. V3: 18.8±0.8%, p<0.001, FIG. 3). Thus, the V1, V2, and V3 peptide fragments are highly effective in inducing cardioprotection against ischemia/reperfusion injuries. Furthermore, when administered after an ischemia/reperfusion injury, all three peptide fragments also induced potent cardioprotection against I/R injury (Control I/R: 37.6±1.3% vs. I/R w. V1: 17.6±3.2% vs. I/R w. V2: 20.6±1.7% vs. I/R w. V3: 15.8±2.0%, p<0.001, FIG. 4). These data demonstrate that these peptide fragments can induce cardioprotection when administered to the heart, before, during, and/or after an ischemia/reperfusion injury. Thus, in some embodiments, V1, V2, and/or V3 peptide fragments may be used to treat acute myocardial infarction in subjects. In some embodiments, the present invention is directed to treating myocardial infarction, reducing or inhibiting infarct size, and/or reducing or inhibiting I/R injury in a subject which comprises administering a therapeutically effective amount of one or more V1, V2, or V3 peptide fragments to the subject, before, during, or after the myocardial infarction or the ischemia or reperfusion.

Figure 5A:
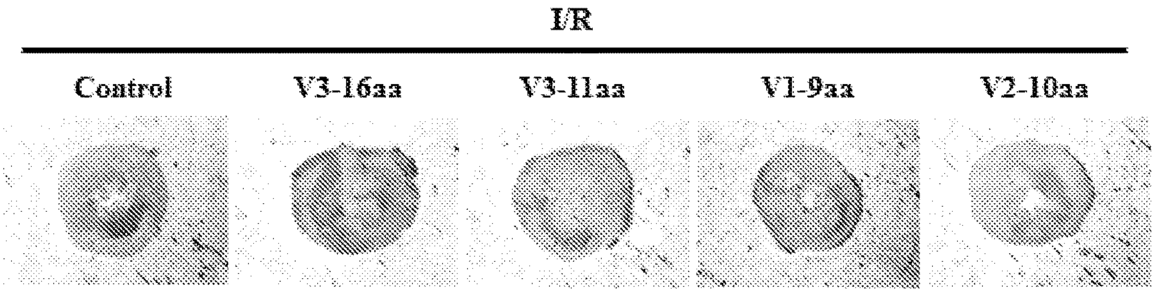
FIGS. 5A-5C show that short netrin-1 peptide fragments containing a core sequence of the netrin-1 Laminin V domain induce potent cardioprotection against ischemia/reperfusion injury post-conditioning. Post-conditioning I/R experiments were performed as illustrated in FIG. 4A. Different peptide fragments V1-9aa, V2-10aa, V3-16aa, and V3-11aa were used at the same molar concentration of 1.47 nmol/L. Sections of hearts were stained with 2,3,5-TTC and infarct area calculated as % of risk area.
Figure 5B:
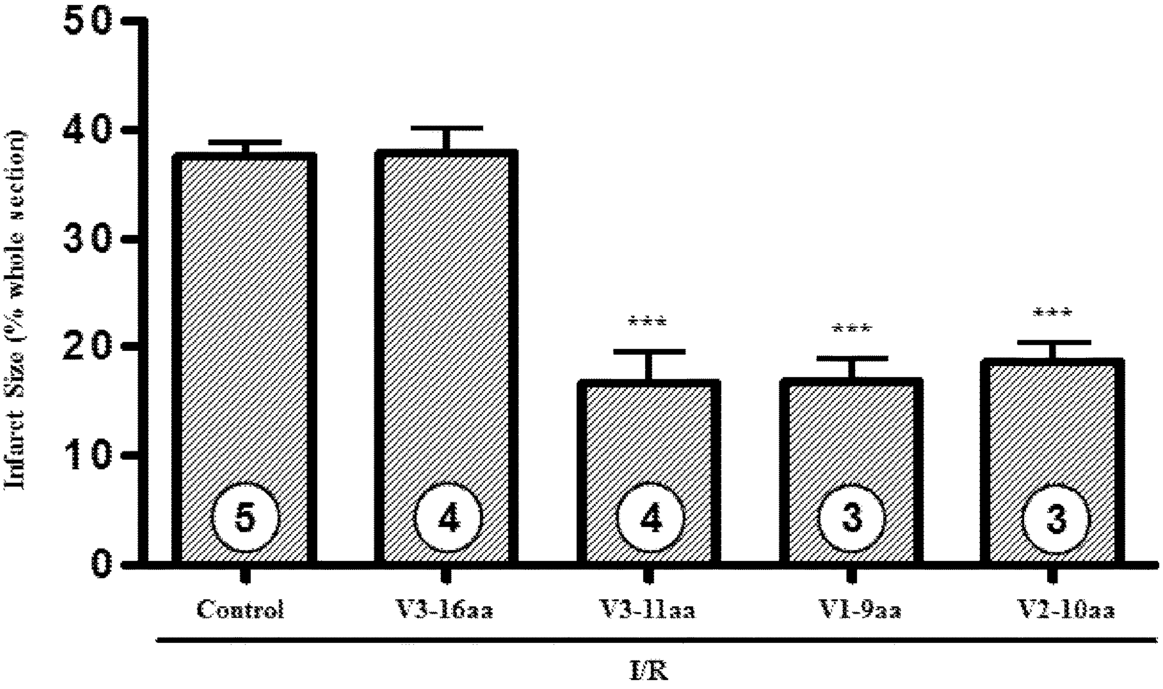
Figure 5C:
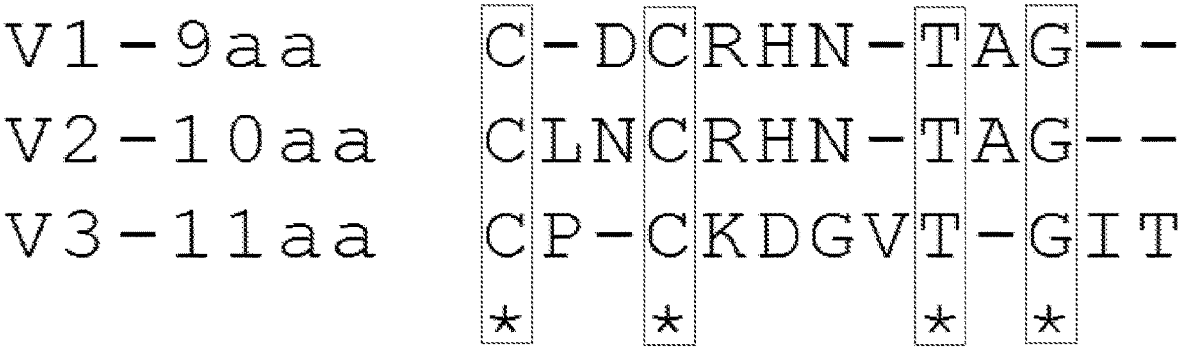

Shorter Truncated Peptide Fragments Effective in Cardioprotection: Identification of Core Sequences The lengths of the V1, V2, and V3 peptide fragments range from 48-61 amino acid residues. In order to find the minimal core sequences which confer cardioprotection, the peptide fragments were aligned and analyzed by ClustalW. Areas of high sequence identity (V1-9aa: residues 304-312; V2-10aa: residues 368-377; V3-11aa: residues 423-433) and a random negative control in V3 domain (V3-16aa: residues 407-422) were synthesized and their activities assayed. As shown in FIGS. 5A and 5B, V1-9aa, V2-10aa, and V3-11aa peptide fragments significantly reduced the infarct size compared to control group (Control I/R: 37.6±1.3% vs. I/R w. V1-9aa: 16.8±2.2%; I/R w. V2-10aa: 18.6±1.7%; I/R 2. V3-11aa: 16.7±3.0%, p<0.001). However, the negative control V3-16aa did not result in significant cardioprotection, and the resulting infarct size was 37.9±2.3%. The amino acid sequences V1-9aa, V2-10aa, and V3-11aa were used to construct Formula I (including Formula IA and Formula IB) and the control peptide, V3-16aa, does not have a sequence which corresponds to Formula I.

Therefore, in some embodiments, peptide fragments which comprise a core sequence according to Formula I, Formula IA, or Formula IB may be used to treat acute myocardial infarction in subjects. In some embodiments, the present invention is directed to treating myocardial infarction, reducing or inhibiting infarct size, and/or reducing or inhibiting I/R injury in a subject which comprises administering a therapeutically effective amount of one or more peptide fragments which comprise a core sequence according to Formula I, Formula IA, or Formula IB to the subject, before, during, or after the myocardial infarction or the ischemia or reperfusion. In some embodiments, the peptide fragments comprising a core sequence according to Formula I, Formula IA, or Formula IB are shorter than V1, V2, and/or V3. In some embodiments, the peptide fragments comprising a core sequence according to Formula I, Formula IA, or Formula IB are 8, 9, 10, or 11 amino acid residues long. In some embodiments, the peptide fragments comprising a core sequence according to Formula I, Formula IA, or Formula IB are 12-47 amino acid residues long. In some embodiments, the peptide fragments comprising a core sequence according to Formula I, Formula IA, or Formula IB are 48-61 amino acid residues long. In some embodiments, the peptide fragments comprising a core sequence according to Formula I, Formula IA, or Formula IB are less than 61 amino acid residues long.

Shorter Peptide Fragments Stimulate Endothelial Cell Nitric Oxide Production

Figure 6A:
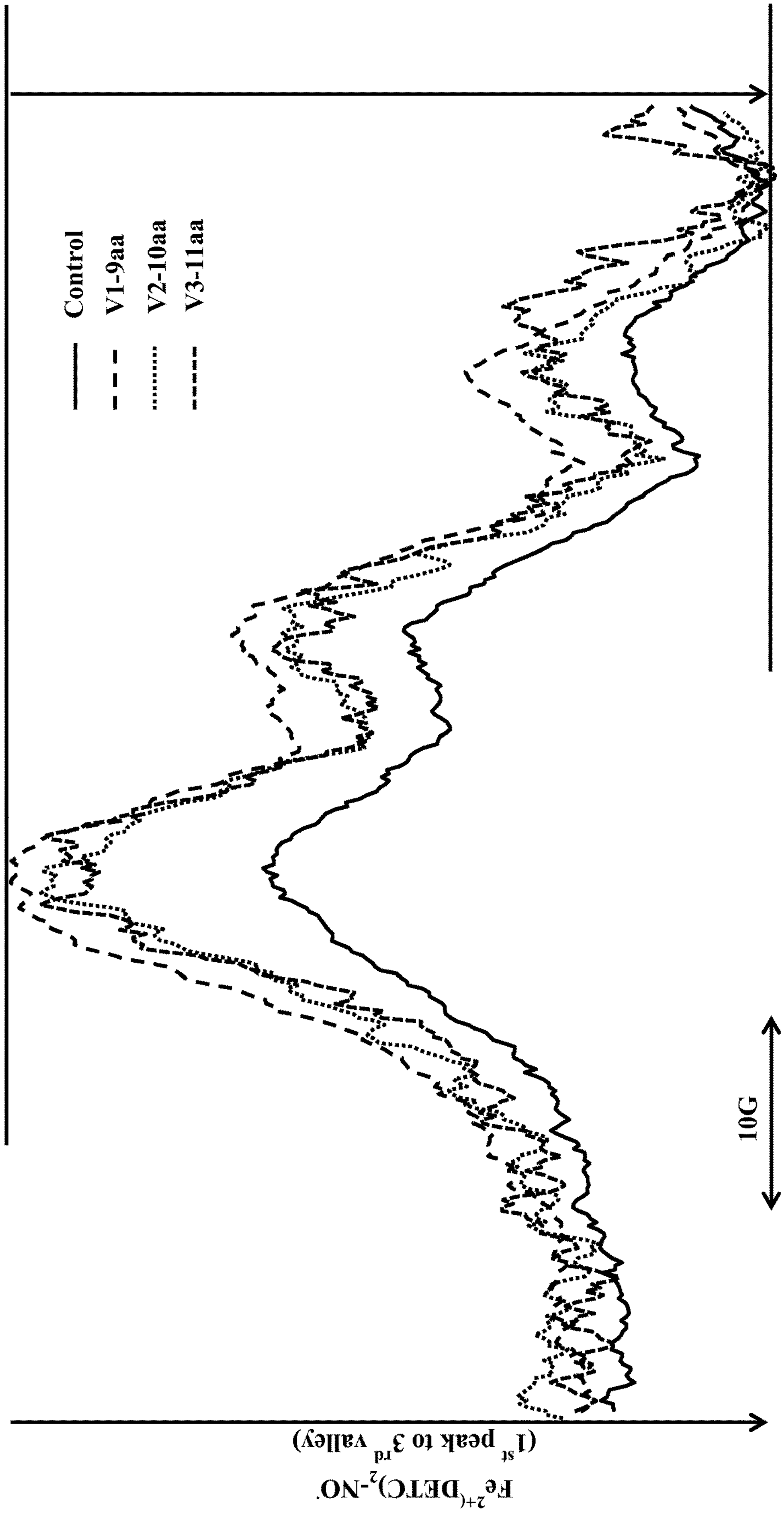
FIGS. 6A and 6B show that short netrin-1 peptide fragments containing a core sequence of the netrin-1 Laminin V domain stimulate endothelial cell nitric oxide production. Confluent endothelial cells were incubated with different peptide fragments V1-9aa, V2-10aa, and V3-11aa at the same molar concentration of 1.47 nmol/L at 37° C. for 60 minutes in modified Krebs/HEPEs buffer containing the NO-specific spin trap $Fe^{2+}(DETC)_2$. Cells were then gently collected for analysis of NO production by using electron spin resonance (ESR).
Figure 6B:
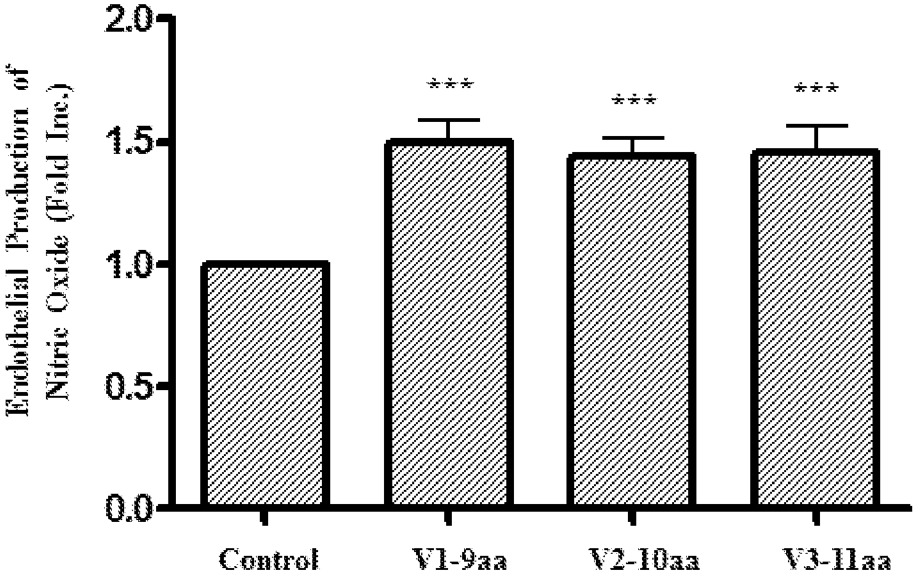

In order to explore the cardioprotective mechanisms of V1-9aa, V2-10aa, and V3-11aa, their effects on endothelial production of NO, which is anticipated to diffuse to cardiomyocytes to activate survival signaling, was examined. As shown in FIG. 6, exposure of endothelial cells to V1-9aa, V2-10aa, and V3-11aa, at the same molar concentration used for netrin-1 perfusion, resulted in significantly elevated NO production (V1-9aa: 1.50±0.09 fold; V2-10aa: 1.44±0.08 fold; V3-11aa: 1.45±0.11 fold, p<0.001). These data indicate that short peptide fragments comprising a core sequence according to Formula I, Formula IA, or Formula IB exhibit potent cardioprotective effects via NO-dependent mechanisms.

Therefore, in some embodiments, peptide fragments which comprise a core sequence according to Formula I, Formula IA, or Formula IB may be used to elevate NO production in subjects. In some embodiments, the present invention is directed to providing cardioprotection to a subject which comprises administering a therapeutically effective amount of one or more peptide fragments which comprise a core sequence according to Formula I, Formula IA, or Formula IB to the subject. In some embodiments, the peptide fragments comprising a core sequence according to Formula I, Formula IA, or Formula IB are 8, 9, 10, or 11 amino acid residues long. In some embodiments, the peptide fragments comprising a core sequence according to Formula I, Formula IA, or Formula IB are 12-47 amino acid residues long. In some embodiments, the peptide fragments comprising a core sequence according to Formula I, Formula IA, or Formula IB are shorter than V1, V2, and/or V3.

Figure 7A:
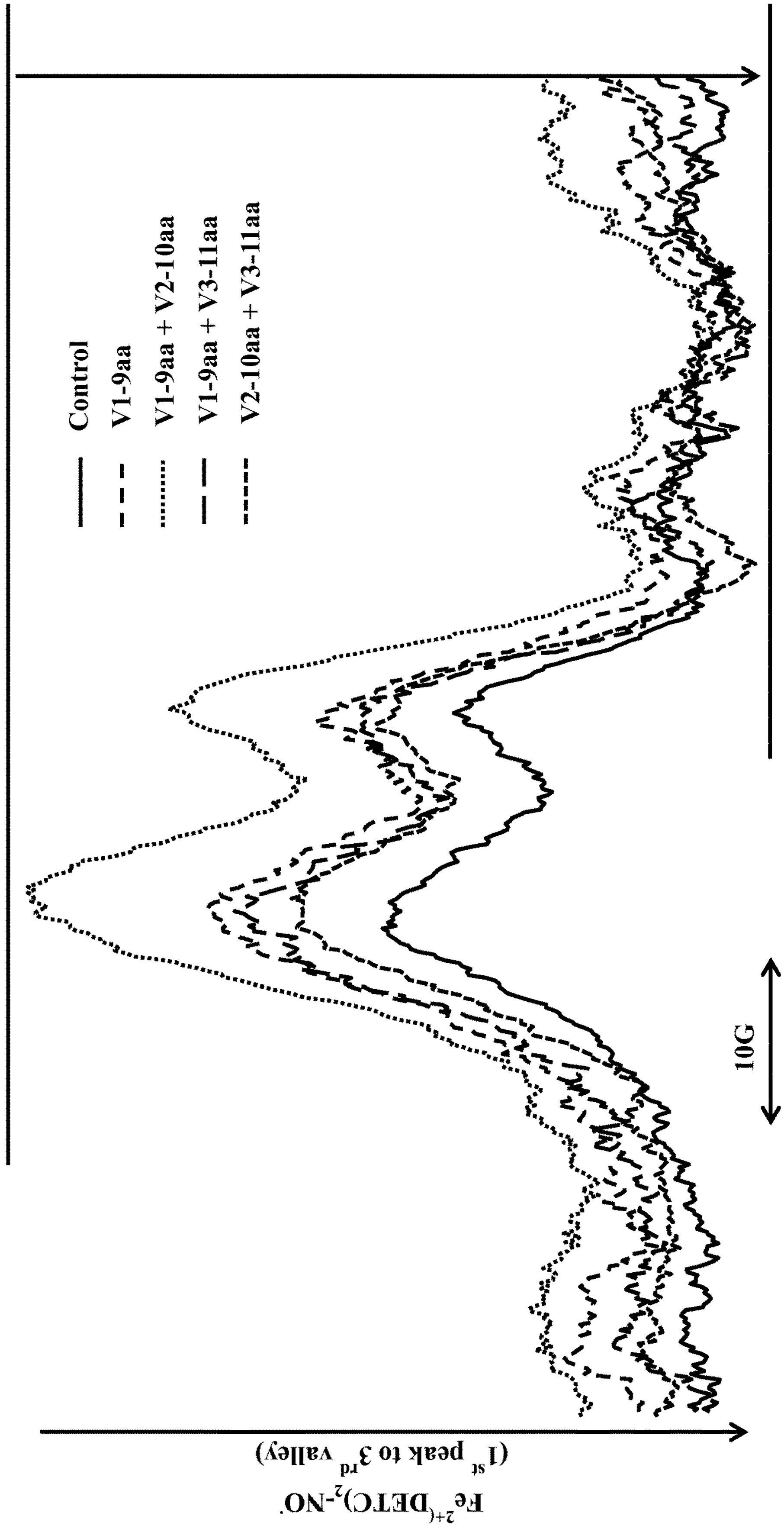
FIGS. 7A and 7B show the effect of the administration of combinations of short netrin-1 peptide fragments containing a core sequence of the netrin-1 Laminin V domain on stimulating endothelial cell NO production. Confluent endothelial cells were incubated with different combination of peptide fragments V1-9aa alone, V1-9aa+V2-10aa (1:1), V1-9aa+V3-11aa (1:1), and V2-10aa+V3-11aa (1:1) at the same total molar concentration of 1.47 nmol/L at 37° C. for 60 minutes in modified Krebs/HEPEs buffer containing the NO-specific spin trap $Fe^{2+}(DETC)_2$. Cells were then gently collected for analysis of NO production by using electron spin resonance (ESR).
Figure 7B:
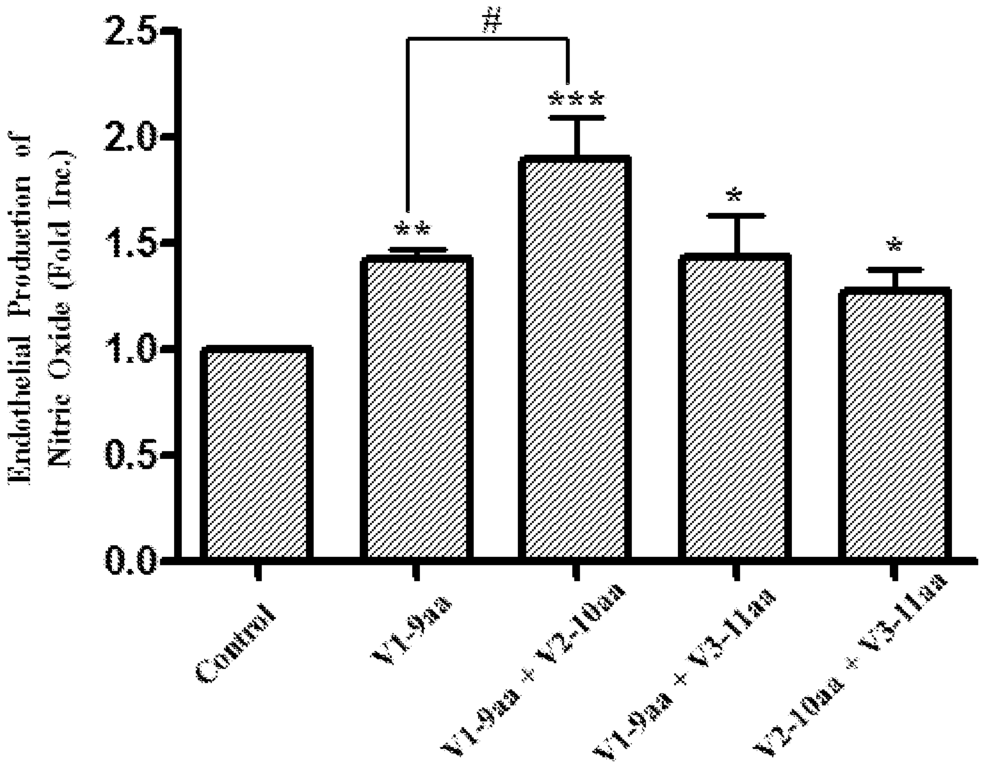

Combinatory Effects of Shorter Peptide Fragments on Stimulating Endothelial Cell Nitric Oxide Production To further identify the synergistic effects peptide fragments according to the present invention, endothelial cells were treated with different combinations of peptide fragments. The treatment groups were: V1-9aa+V2-10aa group, V1-9aa+V3-11aa group, and V2-10aa+V3-11aa group. The amount of each peptide fragment was 50% of the total amount by molar concentration (or equal volume at the same molar concentration) of peptide fragments in the composition, and the final molar concentration was 1.47 nmol/L. Control group (no peptide treatment) and V1-9aa group (1.47 nmol/L) were used to compare with the combination groups. The results, shown in FIG. 7, indicate that the V1-9aa+V2-10aa group produced more NO than the V1-9aa group (V1-9aa+V2-10aa: 1.90±0.50 fold vs. V1-9aa: 1.42±0.18 fold, $p<0.05$). However, the V1-9aa+V3-11aa group and the V2-10aa+V3-11aa group did not show this augmented effect. These data suggest that V1-9aa and V2-10aa shorter peptide fragments can synergistically induce more NO production.

The synergy provided by the combination of V1-9aa+V2-10aa is unexpected as one skilled in the art would have expected the combination to result in approximately a 1.7 fold increase in NO production because (1) physiological regulation of eNOS is generally "modest" and, in contrast, activation of the inducible isoform of NO syntase (iNOS) by inflammatory cytokines would result an increase in NO production of many folds that is toxic, and (2) there was no increase in NO production resulting from the V1-9aa+V3-11aa group and the V2-10aa+V3-11aa group.

Therefore, in some embodiments, a first peptide fragment containing a core sequence according to Formula IA wherein X1 is absent, and a second peptide fragment containing a core sequence according to Formula IA wherein X1 and X2 are present may be co-administered to a subject to elevate NO production in the subject. In some embodiments, the present invention is directed to providing cardioprotection to a subject which comprises co-administering a therapeutically effective amount of a first peptide fragment containing a core sequence according to Formula IA wherein X1 is absent, and a therapeutically effective amount of a second peptide fragment containing a core sequence according to Formula IA wherein X1 and X2 are present to the subject. The amounts of the first and second peptide fragments administered may be synergistic amounts. In some embodiments, the first peptide fragment and/or the second peptide fragment is 8, 9, 10, or 11 amino acid residues long. In some embodiments, the first peptide fragment and/or the second peptide fragment is 12-47 amino acid residues long. In some embodiments, the first peptide fragment and/or the second peptide fragment is shorter than V1, V2, and/or V3. In some embodiments, one of the peptide fragment is V1-9aa. In some embodiments, one of the peptide fragments is V2-10aa. In some embodiments, the first peptide fragment is V1-9aa and the second peptide fragment is V2-10aa.

In some embodiments, the present invention provides compositions comprising or consisting of a first peptide fragment containing a core sequence according to Formula IA wherein X1 is absent, and a second peptide fragment containing a core sequence according to Formula IA wherein X1 and X2 are present. In some embodiments, the first peptide fragment and/or the second peptide fragment is 8, 9, 10, or 11 amino acid residues long. In some embodiments, the first peptide fragment and/or the second peptide fragment is 12-47 amino acid residues long. In some embodiments, the first peptide fragment and/or the second peptide fragment is shorter than V1, V2, and/or V3. In some embodiments, one of the peptide fragment is V1-9aa. In some embodiments, one of the peptide fragments is V2-10aa. In some embodiments, the first peptide fragment is V1-9aa and the second peptide fragment is V2-10aa. In some embodiments, the amount of the first peptide fragment and/or the amount of the second peptide fragment is a therapeutically effective amount. In some embodiments, the combined amount of the first and second peptide fragment is a therapeutically effective amount (e.g., the amount of at least one of the peptide fragments is not a therapeutically effective amount, but the total amount of the first and second peptide fragments together is a therapeutically effective amount). For convenience, such compositions comprising a first peptide fragment and a second peptide fragment as described herein are referred to "synergistic compositions".

In some embodiments, a synergistic composition may be used to elevate NO production in subjects. In some embodiments, the present invention is directed to providing cardioprotection to a subject which comprises administering a therapeutically effective amount of a synergistic composition to the subject.

Materials and Methods

Various methods disclosed in PCT/US2011/038277 may be employed. To the extent necessary PCT/US2011/038277 is herein incorporated by reference in its entirety. Because the experiments herein show that the exemplified peptide fragments containing a core sequence having Formula I, Formula IA, or Formula IB exhibit the same or better activity than netrin-1, other peptide fragments containing the core sequence should similarly exhibit the same or better activity. Additionally, the peptide fragments according to the present invention which comprise, consist essentially of, or consist of a core sequence having Formula I, Formula IA, or Formula IB should also exhibit the same or better therapeutic activity that netrin-1 exhibits. Thus, peptide fragments according to the present invention may be used in place of or to supplement therapeutic treatments employing netrin-1 or other netrin-1 derivatives.

Materials

Purified mouse netrin-1 was purchased from R&D Systems (Minneapolis, Minn., USA). Peptide fragment V1 (285-338 amino acid of human netrin-1), V2 (341-401 aa), V3 (404-451 aa), V1-9aa (304-312 aa), V2-10aa (368-377 aa), V3-16aa (407-422 aa), and V3-11aa (423-433 aa) were synthesized by GenicBio Limited (Shanghai, CHN). Polyclonal antibodies specific for phosphorylated ERK1/2, ERK1/2, and $eNOS_{s1179}$ were obtained from Cell Signaling Technology (Danvers, Mass., USA). Monoclonal antibody for eNOS was purchased from BD Biosciences (San Jose, Calif., USA).

Cell Culture

Bovine aortic endothelial cells (BAECs, Cell Systems, Kirkland, Wash., USA) were cultured in media 199 containing 10% fetal bovine serum (FBS) as previously described. See Chalupsky & Cai, PNAS USA 2005; 102:9056-9061; and Nguyen & Cai, PNAS USA 2006; 103:6530-6535. One day post confluent cells were starved in media containing 5% FBS overnight, then stimulated with netrin-1 protein or different peptide fragments, and harvested at different time points.

Western Blotting

For Western blotting, approximately 20-40 μg of protein was separated by 10% SDS-PAGE, transferred to nitrocellulose membranes, and probed with phosphorylated ERK1/2, ERK1/2, eNOS, and $eNOS_{s1179}$ (1:1,000) antibodies using methods known in the art. See e.g., Gao et al., Journal of Molecular and Cellular Cardiology. 2009; 47:752-760.

Langendorff Perfusion

Male C57BL/6J mice (8-12 weeks old) were obtained from the Charles River Laboratories (Wilmington, Mass., USA). After anesthetized with intraperitoneal pentobarbitone (60 mg/kg), mouse hearts were harvested immediately and the aortas were cannulated with a 20-gauge stainless steel blunt needle and transferred to the Langendorff rig and perfused retrograde instantly with modified Krebs-Henseleit buffer (KHB) for 30 min as previously described. See Bouhidel et al. Front Biosci (Landmark Ed) 2014; 19:566-570, and Zhang et al., J Mol Cell Cardiol. 2010; 48:1060-1070. Then hearts were pre-perfused for 45 minutes with or without netrin-1 (100 ng/ml), or different peptide fragments at the same molar concentration 1.47 nmol/L as netrin-1, prior to being subjected to ischemia/reperfusion (I/R) injury (a 20 minute global ischemia followed by a 60 minute reperfusion with or without netrin-1 or different peptide fragments). Hearts were then harvested for analyses of infarct size. For post-conditioning treatment with peptide fragments, hearts underwent 40 minutes of KHB perfusion, 20 minutes of global ischemia, and a 60 minute reperfusion with different peptide fragments.

Infarct Size Analysis

At the end of I/R protocol, hearts were sliced perpendicular to the long-axis of the heart at 1 mm intervals and stained with 1% triphenyl tetrazolium chloride (TTC) in PBS for 10 minutes at room temperature. After washing with PBS once, sections of the hearts will be fixed in 10% formalin overnight. The heart slices were then digitally photographed for planimetry using NIH Image 1.62. Infarct size is expressed as an infarct-to-risk zone ratio (the risk zone is the whole ventricular volume in this global ischemic model).

Statistical Analysis

Densitometric data of western blotting was obtained by software Image J. Grouped data was analyzed by software Gradpad Prism 6. All values are expressed as Mean±SEM. Comparisons of more than two groups were performed using a one way ANOVA analysis with Newman-Keuls test as a post-hoc test. Statistical significance is set as $p<0.05$.

Examples of Inventive Peptide Fragments

The following are examples of peptide fragments according to the present invention:

V1 (285-338 aa)

(SEQ ID NO: 1)
CKCNGHAARCVRDRDDSLVCDCRHNTAGPECDRCKPFHYDRPWQRATARE

ANEC

V2 (341-401 aa)

(SEQ ID NO: 2)
CNCNLHARRCRFNMELYKLSGRKSGGVCLNCRHNTAGRHCHYCKEGYYRD

MGKPITHRKAC

V3 (404-451 aa)

(SEQ ID NO: 3)
CDCHPVGAAGKTCNQTTGQCPCKDGVTGITCNRCAKGYQQSRSPIAPC

V1-9aa (304-312 aa)

(SEQ ID NO: 4)
CDCRHNTAG

V2-10aa (368-377 aa)

(SEQ ID NO: 5)
CLNCRHNTAG

V3-11aa (423-433 aa)

(SEQ ID NO: 6)
CPCKDGVTGIT

V2-deletion:

(SEQ ID NO: 7)
NLHARRCRFNMELYKLSGRKSGGVCLNCRHNTAGRH

V3-deletion:

(SEQ ID NO: 8)
HPVGAAGKTCNQTTGQCPCKDGVTGIT

The underlined residues in the sequences above indicate the residues falling within Formula I.

As used herein, the amino acid positions indicated are based on the full-length netrin-1 human sequence accession number GI 148613884. Thus, for the negative control V3-16aa, the indicated residues 407-422 are the amino acid residues of GI 148613884, i.e., HPVGAAGKTCNQTTGQ (SEQ ID NO: 9).

Peptide Compositions and Delivery

Administration of one or more peptide fragments according to the present invention can be accomplished by direct administration or accomplished by administering one or more nucleic acid molecules which encode the one or more peptide fragments.

In some embodiments, a therapeutically effective amount of one or more of the peptides fragments according to the present invention are administered to a subject. The term "therapeutically effective amount" as used herein is intended to mean an amount which is effective to alleviate, ameliorate, or prevent a symptom or sign of a disease or condition to be treated. For example, in some embodiments, a therapeutically effective amount is an amount which has a beneficial effect in a subject having signs and/or symptoms of I/R injury of cardiac tissue. In some embodiments, a therapeutically effective amount is an amount which inhibits or reduces signs and/or symptoms of I/R injury as compared to a control. Signs and symptoms of I/R injury to cardiac tissue are well-known in the art and include sudden chest pain (typically radiating to the left arm or left side of the neck), shortness of breath, nausea, vomiting, palpitations, sweating, and anxiety. In some embodiments, the therapeutically effective amount is one which is sufficient to increase nitric oxide production or increase phosphorylation of ERK1/2 and/or eNOS, in a subject as compared to a control. In some embodiments, the therapeutically effective amount is one which is sufficient to activate cardioprotective mechanisms in a subject as compared to a control.

The amount of a composition of the present invention administered to a subject and the route of administration depends on factors such as the severity of an infection affecting the subject, the activity and rate of excretion of one or more peptide fragments according to the present invention, and the general physical characteristics of the subject including age, gender, and body weight. One of skill in the art may readily determine a therapeutically effective amount and route of administration in view of these and other considerations typical in medical practice. Therapeutically effective amounts of one or more peptide fragments according to the present invention may be readily determined by those skilled in the art without undue experimentation.

In general, a therapeutically effective amount of one or more peptide fragments according to the present invention ranges from about 0.001 mg/kg-100 mg/kg body weight, e.g., about 0.01-10 mg/kg to about 0.1-5 mg/kg. A therapeutically effective amount of one or more peptide fragments according to the present invention may be manufactured and/or administered in single or multiple unit dose forms.

In some embodiments, the compositions comprise, consist essentially of, or consist of one or more peptide fragments of the present invention. As used herein, a composition "comprising" one or more peptide fragments according to the present invention means that the composition may contain other compounds, including proteins that are not peptide fragments according to the present invention, e.g., peptide fragments falling within the scope of Formula I, Formula IA, or Formula IB. As used herein, a composition "consisting essentially of" one or more peptide fragments according to the present invention means that the composition may comprise proteins in addition to the peptide fragments according to the present invention so long as the additional proteins do not materially change the activity or function of the peptide fragments according to the present invention that are contained in the composition. As used herein, a composition "consisting of" one or more peptide fragments according to the present invention means that the composition does not contain proteins in addition to the one or more peptide fragments according to the present invention. Compositions consisting of one or more peptide fragments may comprise ingredients other than proteins, e.g., pharmaceutically acceptable carriers, surfactants, preservatives, etc. In some embodiments, compositions consisting of one or more peptide fragments may contain insignificant amounts of contaminants, which may include peptide contaminants, e.g., smaller fragments of the one or more peptide fragments, which may result from, for example, the synthesis of the one or more peptide fragments, subsequent processing, storage conditions, and/or protein degradation.

In some embodiments, the compositions may comprise, consist essentially of, or consist of one or more purified peptide fragments according to the present invention. As used herein, a "purified" peptide fragment means that an amount of the macromolecular components that are naturally associated with the peptide fragment have been removed from the peptide fragment. As used herein, a composition comprising, consisting essentially of, or consisting of one or more purified peptide fragments of the present invention means that the composition does not contain an amount of the macromolecular components that are naturally associated with the one or more peptide fragments and/or the reagents used to synthesize the peptide fragments. In some embodiments, the amount removed from the one or more peptide fragments (or is not present in the composition) is at least about 60%, at least about 70%, at least about 75%, at least about 80%, at least about 85%, at least about 90%, at least about 95%, at least about 96%, at least about 96%, at least about 97%, at least about 98%, at least about 99%, or 100% of the macromolecular components and/or reagents. In some embodiments, the composition is free of at least about 60%, at least about 70%, at least about 75%, at least about 80%, at least about 85%, at least about 90%, at least about 95%, at least about 96%, at least about 96%, at least about 97%, at least about 98%, at least about 99%, or 100% of the macromolecular components naturally associated with the one or more peptide fragments and/or the reagents used to synthesize the one or more peptide fragments. In some embodiments, the compositions of the present invention consist solely of one or more peptide fragments according to the present invention, e.g., the one or more peptide fragments in a solid or crystalized form.

In some embodiments, compositions according to the present invention include one or more peptide fragments according to the present invention and a pharmaceutically acceptable carrier. The term "pharmaceutically acceptable carrier" as used herein refers to a carrier or diluent, which are added to a composition by the hand of man, that is generally non-toxic to an intended recipient and does not significantly inhibit activity of the one or more peptide fragments according to the present invention included in the composition. In some embodiments, compositions according to the present invention may include one or more excipients, diluents, auxiliaries, preservatives, solubilizing agents, buffers, thickening agents, gelling agents, foaming agents, surfactants, binders, suspending agents, disintegrating agents, wetting agents, solvents, plasticizers, fillers, colorants, dispersants, flavoring agents, and/or the like known in the art.

A composition according to the present invention generally includes about 0.1-99% of one or more peptide fragments according to the present invention. In some embodiments, more than one form of the one or more peptide fragments according to the present invention may be provided in the methods and compositions of the present invention. Thus, for example, a peptide fragment derived from human netrin-1 and one or more variants of human netrin-1 or mouse netrin-1 and/or fragments thereof are included in a composition. In some embodiments, the compositions are synergistic compositions, e.g., the compositions comprise a peptide fragment according to the present invention and a second protein which may be a second peptide fragment according to the present invention or, for example, a full length netrin-1 protein, in synergistic amounts.

In some embodiments, one or more peptide fragments according to the present invention are included in a composition of the present invention in the form of a free acid or free base. In some embodiments, one or more peptide fragments according to the present invention are included in a composition in the form of a pharmaceutically acceptable salt such as an acid or base addition salt. A pharmaceutically acceptable salt refers to any salt form of the one or more peptide fragments according to the present invention that is generally non-toxic to an intended recipient and does not significantly inhibit activity of the one or more peptide fragments according to the present invention or other active agent included in the composition. In some embodiments, the one or more peptide fragments according to the present invention are provided in the form of a hydrate or a prodrug.

A composition including one or more peptide fragments according to the present invention may be administered by a systemic route and/or by a local route. Suitable routes of administration illustratively include intravenous, oral, buccal, parenteral, intrathecal, intracerebroventricular, intraperitoneal, intracardiac, intraarterial, intravesicle, ocular, intraocular, rectal, vaginal, subcutaneous, intradermal, transdermal, intramuscular, topical, intranasal, and transmucosal. In some embodiments, the one or more peptide fragments according to the present invention and compositions thereof are administered intravenously or by intraventricular injection, e.g., during angioplasty for acute MI treatment or open heart surgery.

In some embodiments, the peptide fragments and compositions according to the present invention may be modified using methods and compositions known in the art to improve their biological half-life, stability, efficacy, bioavailability, bioactivity, or a combination thereof.

For example, in some embodiments, the peptide fragments may be subjected to cyclization to result in a cyclic peptide which is resistant to proteolytic degradation. Cyclization may be carried out between side chains or ends of the peptide sequences through disulfide bonds, lanthionine, dicarba, hydrazine, or lactam bridges using methods known in the art.

In some embodiments, the peptide fragments may be conjugated to a molecule such as vitamin B12, a lipid, or an ethylene oxide compound, e.g., polyethylene glycol (PEG), polyethylene oxide (PEO), and polyoxyethylene (POE), methoxypolyethylene glycol (MPEG), mono-methoxy PEG (mPEG), and the like. The ethylene oxide compound may be further functionalized with, for example, amine binding terminal functional groups such as N-hydroxysuccinimide esters, N-hydroxysuccinimide carbonates, and aliphatic aldehyde, or thiol binding groups such as maleimide, pyridyl disulphides, and vinyl sulfonates. Since amino groups (α-amino and ε-lysine amino) and cysteine residues are well suited for conjugation, the peptide fragments according to the present invention may further include one or more amino acid residues for conjugation to an ethylene oxide molecule or a carrier compound known in the art. The pharmacokinetic and pharmacodynamic properties of a conjugated peptide may be further modified by the use of a particular linker. For example, propyl and amyl linkers can be used to provide a conjugate having a loose conformation whereas a phenyl linker may be used to provide a denser conformation as well as shield domains adjacent to the C-terminus. It is noted that dense conformations are generally more efficient in maintaining bioactivity, prolonging plasma half-life, lowering proteolytic sensitivity, and immunogenicity relative to loose conformations.

In some embodiments, the peptide fragments may be hyperglycosylated using methods known in the art, e.g., in situ chemical reactions or site-directed mutagenesis. Hyperglycosylation may result in either N-linked or O-linked protein glycosylation. The clearance rate of a given peptide fragment may be optimized by the selection of the particular saccharide. For example, polysialic acid (PSA) is available in different sizes and its clearance depends on type and molecular size of the polymer. Thus, for example, PSAs having high molecular weights may be suitable for the delivery of low-molecular-weight peptide fragments, and PSAs having low molecular weights may be suitable for the delivery of peptide fragments having high molecular weights. The type of saccharide can be used to target the peptide to a particular tissue or cell. For example, peptide fragments conjugated with mannose can be recognized by mannose-specific lectins, e.g., mannose receptors and mannanbinding proteins, and are taken up by the liver. In some embodiments, the peptide fragments may be hyperglycosylated to improve their physical and chemical stability under different environmental conditions, e.g., to inhibit inactivation under stress conditions and reduce aggregation resulting from production and storage conditions.

In some embodiments, a drug delivery system, such as microparticles, nanoparticles (particles having sizes ranging from 10 to 1000 nm), nanoemulsions, liposomes, and the like, may be used to provide protection of sensitive proteins, prolong release, reduce administration frequency, increase patient compliance, and control plasma levels. Various natural or synthetic microparticles and nanoparticles, which may be biodegradable and/or biocompatible polymers, may be used. Microparticles and nanoparticles can be fabricated from lipids, polymers, and/or metal. Polymeric microparticles and nanoparticles may be fabricated from natural or synthetic polymers, such as starch, alginate, collagen, chitosan, polycaprolactones (PCL), polylactic acid (PLA), poly (lactide-co-glycolide) (PLGA), and the like. In some embodiments, the nanoparticles are solid lipid nanoparticles (SLNs), carbon nanotubes, nanospheres, nanocapules, and the like. In some embodiments, the polymers are hydrophilic. In some embodiments, the polymers are thiolated polymers.

Since the rate and extent of drug release from microparticles and nanoparticles may depend on the composition of polymer and fabrication methods one may select a given composition and fabrication method, e.g., spray drying, lyophilization, microextrusion, and double emulsion, to confer a desired drug release profile. Since peptide fragments incorporated in or on microparticles or nanoparticles may be prone to denaturation at aqueous-organic interface during formulation development, different stabilizing excipients and compositions can be used to prevent aggregation and denaturation. For example, PEG and sugars, e.g., PEG (MW 5000) and maltose with α-chymotrypsin, may be added to the composition to reduce aggregation and denaturation. Additionally, chemically modified peptide fragments, e.g., conjugated peptide fragments and hyperglycosylated peptide fragments, may be employed.

Protein stability can also be achieved by the selected fabrication method. For example, to prevent degradation at aqueous-organic interface, non-aqueous methodology called ProLease® technology may be used. Peptide fragments in solid state can also be encapsulated using solid-in-oil-in-water (s/o/w) methods, e.g., spray- or spray-freeze-dried peptide fragments or peptide-loaded solid nanoparticles can be encapsulated in microspheres using s/o/w methods. Hydrophobic ion-pairing (HIP) complexation may be used to enhance protein stability and increase encapsulation efficiency into microparticles and nanoparticles. In hydrophobic ion-pairing (HIP) complexation, ionizable functional groups of a peptide are complexed with ion-pairing agents (e.g., surfactant or polymer) containing oppositely charged functional groups leading to formation of HIP complex where hydrophilic protein molecules exist in a hydrophobic complex form.

In some embodiments, liposomes of either synthetic or natural origin and various sizes, e.g., 20 nm to several hundred micrometers, may be used to deliver the peptide fragments according to the present invention. Depending on the preparation method, the liposomes can be small unilamellar vesicles (25-50 nm), large unilamellar vesicles (100-200 nm), giant unilamellar vesicles (1-2 μm), and multilamellar vesicles (MLV; 1 μm-2 μm). The peptide fragments being delivered can be either encapsulated into liposomes or adsorbed on the surface. The size and surface properties of liposomes may be optimized for a desired result. For example, unilamellar and multilamellar liposomes provide sustained release from several hours to days after intravascular administration. The prolonged drug release can be achieved by multivesicular liposomes, also known as DepoFoam® technology. Unlike ULV and MLV, multivesicular liposomes are composed of nonconcentric multiple aqueous chambers surrounded by a network of lipid layers which confers an increased level of stability and longer duration of drug release. The liposomes may be further modified to achieve a desired result. For example, the liposomes may be PEGylated or have other surface modifications in order to interfere with recognition and uptake by the reticuloendothelial system and provide increased circulation times.

Exemplary liposomes suitable for use according to the present invention include multilamellar vesicles (MLV), oligolamellar vesicles (OLV), unilamellar vesicles (UV), small unilamellar vesicles (SUV), medium-sized unilamellar vesicles (MUV), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV).

The liposomes may comprise additional lipids, e.g., carrier lipids, including palmitoylphosphatidylcholine (DPPC), phosphatidylcholine (PC; lecithin), phosphatidic acid (PA), phosphatidylglycerol (PG), phosphatidylethanolamine (PE), phosphatidylserine (PS), distearoylphosphatidylcholine (DSPC), dimyristoylphosphatidylcholine (DMPC), dipalmitoylphosphatidyglycerol (DPPG), distearoylphosphatidyglycerol (DSPG), dimyristoylphosphatidylglycerol (DMPG), dipalmitoylphosphatidic acid (DPPA); dimyristoylphosphatidic acid (DMPA), distearoylphosphatidic acid (DSPA), dipalmitoylphosphatidylserine (DPPS), dimyristoylphosphatidylserine (DMPS), distearoylphosphatidylserine (DSPS), dipalmitoylphosphatidyethanolamine (DPPE), dimyristoylphosphatidylethanolamine (DMPE), distearoylphosphatidylethanolamine (DSPE), and the like, or combinations thereof. In some embodiments, the liposomes further comprise a sterol (e.g., cholesterol).

In some embodiments, micelles may be used to deliver the peptide fragments according to the present invention. Phospholipids such as DSPE-PEG, co-polymeric systems PEG-PE, PLA-PEG and hyperbranched poly([amine-ester]-co-[d, l-lactide]) and polyion complexes may be used to increase stability and pharmacokinetics.

Thermosensitive gels may be used to deliver the peptide fragments according to the present invention. Thermoreversible block copolymers comprising PEG, PCL, PLA, poly (glycolide), PLGA, poly (N-isopropylacrylamide), polyethylene oxide, chitosan, and the like may be used to provide controlled release of the peptide fragments. Examples of thermosensitive gels include PLGA-PEG-PLGA triblock copolymer gels and Pluronic F-127 (PF127). Polyelectrolyte complexes and/or PEGylation may be used to provide sustained release of proteins from the gels. Microparticles and/or nanoparticles may also be used in combination with gels to provide sustained drug delivery.

Peptide fragments according to the present invention may be chemically synthesized, or recombinantly expressed in a cell system or a cell-free system. Synthetic methods include liquid-phase synthesis, solid-phase synthesis, and microwave assisted peptide synthesis. The peptide fragments may be modified by acylation, alkylation, amidation, arginylation, polyglutamylation, polyglycylation, butyrylation, gamma-carboxylation, glycosylation, malonylation, hydroxylation, iodination, nucleotide addition (e.g., ADP-ribosylation), oxidation, phosphorylation, adenylylation, propionylation, S-glutathionylation, S-nitrosylation, succinylation, sulfation, glycation, palmitoylation, myristoylation, isoprenylation or prenylation (e.g., farnesylation or geranylgeranylation), glypiation, lipoylation, attachement of flavin moiety (e.g., FMN or FAD), attachment of heme C, phosphopantetheinylation, retinylidene Schiff base formation, diphthamide formation, ethanolamine phosphoglycerol attachment, hypusine formuation, biotinylation, pegylation, ISGylation, SUMUylation, ubiquitination, Neddylation, Pupylation, citrullination, deamidation, eliminylation, carbamylation, or a combination thereof.

Compositions comprising one or more peptide fragments according to the present invention may be subjected to one or more rounds of purification or concentration steps known in the art to remove impurities and/or concentrate the peptide fragments. Thus, in some embodiments, the present invention provides peptide compositions having a purity and/or composition not found in nature. In some cases, the peptide composition is at most 30%, 40%, 50%, 60%, 70%, 80%, 90%, 95%, 99%, 99.9%, or 100% pure peptide fragments. In some cases, the peptide composition is at least 30%, 40%, 50%, 60%, 70%, 80%, 90%, 95%, 99%, 99.9%, or 100% pure peptide fragments. In some cases, the composition is free of impurities. In some cases, the amount of the peptide fragments in the peptide composition is at most 30%, 40%, 50%, 60%, 70%, 80%, 90%, 95%, 99%, 99.9%, or 100% weight of the total composition. In some cases, the amount of the peptide fragments in the peptide composition is at least 30%, 40%, 50%, 60%, 70%, 80%, 90%, 95%, 99%, 99.9%, or 100% by weight of the total composition.

Exemplary Additional Embodiments

The following are exemplary embodiments according to the present invention and are in addition to that described in the specification and the claims appended hereto.

Embodiment 1. A peptide that is 8-65 amino acid residues in length and having a sequence having formula $CX_{(1-2)}CX_{(3-4)}TX_{(0-1)}G$ (SEQ ID NO: 10) (Formula A) or $CX_{(1-2)}$ CRHNTAG (SEQ ID NO: 12) (Formula B), where X is any residue, or Formula I, Formula IA, or Formula IB.

Embodiment 2. The peptide of Embodiment 1, wherein the peptide has up to 99% sequence identity to netrin-1.

Embodiment 3. The peptide of Embodiment 2, wherein the netrin-1 is mouse or human netrin-1.

Embodiment 4. The peptide of any one of Embodiments 1-3, wherein the length of the peptide is about 8-55, about 8-50, about 8-35, about 8-30, about 8-20, about 8-15, about 8-12, or 9-11 amino acid residues in length.

Embodiment 5. A peptide selected from the group consisting of V1, V2, V3, V2-deletion, V3-deletion, and V3-2 (V3-11aa).

Embodiment 7. A composition comprising a concentrated amount of one or more peptides according to any one of Embodiments 1-5.

Embodiment 8. The composition according to Embodiment 7, wherein the concentrated amount is a concentration not found in nature.

Embodiment 9. A man-made package comprising therein one or more peptides according to Embodiments 1-5 or the composition according to Embodiment 7 or Embodiment 8.

Embodiment 10. A method of decreasing or reducing the infarct size of a heart resulting from ischemia/reperfusion injury which comprises contacting the heart with one or more peptides according to Embodiments 1-5 or the composition according to Embodiment 7 or Embodiment 8; attenuating superoxide production in the heart by contacting the heart with one or more peptides according to Embodiments 1-5 or the composition according to Embodiment 7 or Embodiment 8; attenuating NOX4 expression in the heart by contacting the heart with one or more peptides according to Embodiments 1-5 or the composition according to Embodiment 7 or Embodiment 8; reducing NOS uncoupling in the heart by contacting the heart with one or more peptides according to Embodiments 1-5 or the composition according to Embodiment 7 or Embodiment 8; increasing NOS recoupling in the heart by contacting the heart with one or more peptides according to Embodiments 1-5 or the composition according to Embodiment 7 or Embodiment 8; or a combination thereof.

Embodiment 11. A method of treating, inhibiting, or reducing ischemia/reperfusion injury of a cardiac tissue which comprises increasing nitric oxide production in the cardiac tissue by stimulating DCC-dependent activation of ERK1/2 and eNOS by contacting the cardiac tissue with one or more peptides according to Embodiments 1-5 or the composition according to Embodiment 7 or Embodiment 8.

Embodiment 12. A method of treating, inhibiting, or reducing loss of NO by a cardiac tissue resulting from ischemia/reperfusion injury and/or decreasing or reducing superoxide production by a cardiac tissue resulting from ischemia/reperfusion injury which comprises contacting the cardiac tissue with one or more peptides according to Embodiments 1-5 or the composition according to Embodiment 7 or Embodiment 8.

Embodiment 13. A method of increasing NO production; increasing phosphorylation of ERK1/2 and/or eNOS; treating, inhibiting, or reducing loss of DCC protein and mRNA expression; treating, inhibiting, or reducing loss of eNOS protein expression; or a combination thereof, in a cardiac tissue which comprises contacting the cardiac tissue with one or more peptides according to Embodiments 1-5 or the composition according to Embodiment 7 or Embodiment 8.

Embodiment 14. A method of treating, inhibiting, or reducing NOS uncoupling; increasing NOS recoupling; decreasing mitochondrial damage resulting from ischemia/reperfusion injury; or a combination thereof, which comprises contacting the heart with one or more peptides according to Embodiments 1-5 or the composition according to Embodiment 7 or Embodiment 8, sepiapterin, or both.

Embodiment 15. A method of decreasing mitochondrial damage resulting from ischemia/reperfusion injury which comprises attenuation of NOX4 expression via contacting the heart with one or more peptides according to Embodiments 1-5 or the composition according to Embodiment 7 or Embodiment 8.

Embodiment 16. A method of treating, inhibiting, or reducing ischemia/reperfusion injury of a cardiac tissue which comprises reducing or inhibiting NOX4 expression by contacting the cardiac tissue with siRNA alone or in combination with one or more peptides according to Embodiments 1-5 or the composition according to Embodiment 7 or Embodiment 8.

Embodiment 17. The method according to any one of the preceding Embodiments, wherein the cardiac tissue is contacted with one or more peptides according to Embodiments 1-5 or the composition according to Embodiment 7 or Embodiment 8 before, during, or after being subjected to a condition, such as surgery, inflammation and pharmacological agents that decrease NO, decrease DCC-dependent signaling, decrease ERK1/2-dependent signaling, decrease eNOS phosphorylation at serine 1177; increase superoxide, increase NOX4, increase NOS uncoupling, increase mitochondrial damage, which results in the ischemia/reperfusion injury.

Embodiment 18. A method of treating, inhibiting, or reducing neointimal formation and restenosis which comprises contacting blood vessels with one or more peptides according to Embodiments 1-5 or the composition according to Embodiment 7 or Embodiment 8 systematically or locally; attenuating vascular smooth muscle cell migration and proliferation with one or more peptides according to Embodiments 1-5 or the composition according to Embodiment 7 or Embodiment 8; attenuating vascular smooth muscle cell migration and proliferation with one or more peptides according to Embodiments 1-5 or the composition according to Embodiment 7 or Embodiment 8 via DCC-dependent signaling; activating DCC in vascular smooth muscle by contacting with one or more peptides according to Embodiments 1-5 or the composition according to Embodiment 7 or Embodiment 8; or a combination thereof.

Embodiment 19. A method of treating, inhibiting, or reducing vascular diseases involving vascular injury such as atherosclerosis and hypertension which comprises contacting blood vessels with one or more peptides according to Embodiments 1-5 or the composition according to Embodiment 7 or Embodiment 8 systematically or locally; attenuating vascular smooth muscle cell migration and proliferation with one or more peptides according to Embodiments 1-5 or the composition according to Embodiment 7 or Embodiment 8 via DCC-dependent signaling; or both.

Embodiment 20. A method of treating, inhibiting, or reducing vascular dysfunction characterized by vascular smooth muscle cell proliferation and migration; treating, inhibiting, or preventing vascular diseases characterized by vascular smooth muscle cell proliferation and migration such as aneurysms of any vascular beds of systematic or cerebral; or both which comprises contacting blood vessels with one or more peptides according to Embodiments 1-5 or the composition according to Embodiment 7 or Embodiment 8 systematically or locally.

Embodiment 21. A method of treating, inhibiting, or reducing vascular diseases involving vascular injury such as atherosclerosis and hypertension; treating, inhibiting, or reducing vascular dysfunction characterized by vascular smooth muscle cell proliferation and migration; treating, inhibiting, or preventing vascular diseases characterized by vascular smooth muscle cell proliferation and migration such as aneurysms of any vascular beds such as systematic and cerebral, or a combination thereof, which comprises activating DCC in vascular smooth muscle by contacting with one or more peptides according to Embodiments 1-5 or the composition according to Embodiment 7 or Embodiment 8.

Embodiment 22. A method of treating, inhibiting, or reducing apoptosis of endothelial progenitor cells resulting from exposure to oxidative stress which comprises contacting the endothelial progenitor cells with one or more peptides according to Embodiments 1-5 or the composition according to Embodiment 7 or Embodiment 8.

Embodiment 23. A method of improving quality of endothelial progenitor cells prior to cell-based therapies for any condition requiring endothelial progenitor cell treatment including both vascular and cardiac diseases which comprises contacting the endothelial progenitor cells with one or more peptides according to Embodiments 1-5 or the composition according to Embodiment 7 or Embodiment 8 to pre-condition endothelial cells prior to being used for cell-based therapies.

Embodiment 24. A method of treating, inhibiting, or reducing neointimal formation and restenosis, or a combination thereof of a blood vessel (such as an artery, a coronary artery, a vein, or a capillary) or a portion of the blood vessel which comprises contacting the blood vessel or the portion of the blood vessel with one or more peptides according to Embodiments 1-5 or the composition according to Embodiment 7 or Embodiment 8 before, during, or after the blood vessel is subjected to a condition, such as surgery, inflammation and pharmacological agents that decrease NO, increase superoxide, increase vascular smooth muscle migration and proliferation, which results in the neointimal formation and restenosis.

Embodiment 25. A method of treating, inhibiting, or reducing apoptosis of endothelial progenitor cells, or a combination thereof of a blood vessel (such as an artery, a coronary artery, a vein, or a capillary) or a portion of the blood vessel which comprises contacting the blood vessel or endothelial progenitor cells with one or more peptides according to Embodiments 1-5 or the composition according to Embodiment 7 or Embodiment 8 before, during, or after the blood vessel is subjected to a condition, such as surgery, inflammation and pharmacological agents that decrease NO, increase superoxide and hydrogen peroxide, which results in apoptosis of endothelial progenitor cells.

Embodiment 26. The method according to any one of the preceding Embodiments, wherein one or more peptides according to Embodiments 1-5 or the composition according to Embodiment 7 or Embodiment 8 is contacted with the cardiac tissue or heart by administering the one or more peptides or the composition to a subject, preferably a mammalian subject, more preferably a human subject, having the cardiac tissue or heart.

Embodiment 27. The method according to any one of the preceding Embodiments, wherein the cardiac tissue is a heart, cardiomyocytes, or cardiac endothelial cells.

Embodiment 28. The method according to any one of the preceding Embodiments, wherein the one or more peptides or the composition is contacted with the cardiac tissue, heart, blood vessels, endothelial progenitor cells, or the vascular smooth muscle cells in vitro or in vivo.

Embodiment 29. The method according to any one of the preceding Embodiments, wherein the one or more peptides or the composition is contacted with the cardiac tissue, heart, blood vessels, endothelial progenitor cells, or the vascular smooth muscle cells systematically or locally.

Embodiment 30. The method according to any one of the preceding Embodiments, wherein the amount the one or more peptides or the composition is a therapeutically effective amount.

Embodiment 31. The method according to any one of the preceding Embodiments, which further comprises contacting the cardiac tissue, heart, blood vessels, endothelial progenitor cells, or the vascular smooth muscle cells with sepiapterin.

Embodiment 32. Use of one or more peptides according to Embodiments 1-5 or the composition according to Embodiment 7 or Embodiment 8 for the manufacture of a medicament for treating, inhibiting, or reducing ischemia/reperfusion injury of a cardiac tissue; increasing phosphorylation of ERK1/2 and/or eNOS in a cardiac tissue; treating, inhibiting, or reducing loss of NO; treating, inhibiting, or reducing loss of DCC protein and mRNA expression in a cardiac tissue; treating, inhibiting, or reducing loss of eNOS protein expression in a cardiac tissue; decreasing or reducing the infarct size of a heart resulting from ischemia/reperfusion injury; decreasing or reducing superoxide production by a cardiac tissue caused by ischemia/reperfusion injury; treating, inhibiting, or reducing NOX4 upregulation in a cardiac tissue; treating, inhibiting, or reducing loss of NOS uncoupling in a cardiac tissue; increasing NOS recoupling in a cardiac tissue; treating, inhibiting, or reducing mitochondrial damage in a cardiac tissue; treating, inhibiting, or reducing neointimal formation and restenosis; treating, inhibiting, or reducing vascular smooth muscle cell proliferation and migration; increasing vascular smooth muscle cell DCC activation; treating, inhibiting, or reducing apoptosis of endothelial progenitor cells; increasing endothelial cell progenitor survival by pre-conditioning; or a combination thereof of a blood vessel (such as an artery, a coronary artery, a vein, or a capillary) or a portion of the blood vessel in a subject, preferably a mammalian subject, more preferably a human subject.

Embodiment 33. Use of one or more peptides according to Embodiments 1-5 or the composition according to Embodiment 7 or Embodiment 8 for the manufacture of a medicament for treating, inhibiting, or reducing ischemia/reperfusion injury of a cardiac tissue; increasing phosphorylation of ERK1/2 and/or eNOS in a cardiac tissue; treating, inhibiting, or reducing loss of NO; treating, inhibiting, or reducing loss of DCC protein and mRNA expression in a cardiac tissue; treating, inhibiting, or reducing loss of eNOS protein expression in a cardiac tissue; decreasing or reducing the infarct size of a heart resulting from ischemia/reperfusion injury; decreasing or reducing superoxide production by a cardiac tissue caused by ischemia/reperfusion injury; treating, inhibiting, or reducing NOX4 upregulation in a cardiac tissue; treating, inhibiting, or reducing loss of NOS uncoupling in a cardiac tissue; increasing NOS recoupling in a cardiac tissue; treating, inhibiting, or reducing mitochondrial damage in a cardiac tissue; treating, inhibiting, or reducing neointimal formation and restenosis; treating, inhibiting, or reducing vascular smooth muscle cell proliferation and migration; increasing vascular smooth muscle cell DCC activation; treating, inhibiting, or reducing apoptosis of endothelial progenitor cells; increasing endothelial cell progenitor survival by pre-conditioning; or a combination thereof of a blood vessel (such as an artery, a coronary artery, a vein, or a capillary) or a portion of the blood vessel in a subject, preferably a mammalian subject, more preferably a human subject, wherein the medicament is prepared to be administered as a single dose or as several doses.

Section headings are used for organizational purposes only and are not to be construed as defining or limiting the subject matter described. Unless explicitly provided otherwise, singular word forms include the plural forms. As used herein, the singular forms "a", "an", and "the" include plural referents unless the context clearly dictates otherwise. As used herein, "and/or" means "and" or "or". For example, "A and/or B" means "A, B, or both A and B" and "A, B, and/or C" means "A, B, C, or a combination thereof" and said "combination thereof" means "A and B, A and C, or B and C". As used herein, "or" can mean "and/or" unless stated otherwise or the context clearly dictates otherwise.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A peptide consisting of 8-35 amino acid residues and having a core sequence represented by Formula IA as follows:

C-X1-X2-C-X3-X4-X5-X6-T-X7-G (SEQ ID NO: 11) (IA)

wherein

X1 may be present or absent, and if present, X1 is selected from the group consisting of A, V, L, I, P, F, M, and W;

X2 may be present or absent, and if present, X2 is selected from the group consisting of D, E, G, N, Q, S, T, Y, and C;

X3 is selected from the group consisting of K, R, and H;

X4 is selected from the group consisting of D, E, K, R, H, Y, F, and W;

X5 is selected from the group consisting of G, N, Q, S, T, Y, and C;

X6 may be present or absent and if present, X6 is selected from the group consisting of T, V, and I; and X7 may be present or absent, and if present, X7 is selected from the group consisting of A, V, L, I, P, F, M, and W; and wherein either X1, X2, or both X1 and X2 are present; wherein the peptide has improved efficacy in reducing ischemia/reperfusion injury or reducing infarct size as compared to netrin-1.

2. The peptide according to claim 1 wherein the core sequence is represented by Formula IB as follows:

C-X1-X2-C-R-H-N-T-A-G (SEQ ID NO: 12) (IB)

wherein

X1 may be present or absent, and if present, X1 is selected from the group consisting of A, V, L, I, P, F, M, and W; and X2 may be present or absent, and if present, X2 is selected from the group consisting of D, E, G, N, Q, S, T, Y, and C; and wherein either X1, X2, or both X1 and X2 are present.

3. The peptide according to claim 2, wherein at least one amino acid residue is different from the corresponding amino acid residue of a naturally occurring netrin-1 protein sequence.

4. The peptide according to claim 3, wherein the peptide is about 8-30, about 8-20, about 8-15, about 8-12, 8-11, about 9-30, about 9-20, about 9-15, about 9-12, or 9-11 amino acid residues long.

5. The peptide according to claim 4, wherein the peptide is 8, 9, 10, or 11 amino acid residues long.

6. The peptide according to claim 1, wherein the peptide is about 8-30, about 8-20, about 8-15, about 8-12, 8-11, about 9-30, about 9-20, about 9-15, about 9-12, or 9-11 amino acid residues long.

7. The peptide according to claim 1, wherein the peptide is 8, 9, 10, or 11 amino acid residues long.

8. The peptide according to claim 1, wherein at least one amino acid residue is different from the corresponding amino acid residue of a naturally occurring netrin-1 protein sequence.

9. The peptide according to claim 1, wherein the amino acid sequence is SEQ ID NO: 4, SEQ ID NO: 5, SEQ ID NO: 6, SEQ ID NO: 7, or SEQ ID NO: 8.

10. A composition comprising a first peptide and a second peptide, wherein the first and second peptides each independently consist of 8-35 amino acid residues and having a core sequence represented by Formula IA as follows:

C-X1-X2-C-X3-X4-X5-X6-T-X7-G (SEQ ID NO: 11) (IA)

wherein

X1 may be present or absent, and if present, X1 is selected from the group consisting of A, V, L, I, P, F, M, and W;

X2 may be present or absent, and if present, X2 is selected from the group consisting of D, E, G, N, Q, S, T, Y, and C;

X3 is selected from the group consisting of K, R, and H;

X4 is selected from the group consisting of D, E, K, R, H, Y, F, and W;

X5 is selected from the group consisting of G, N, Q, S, T, Y, and C;

X6 may be present or absent and if present, X6 is selected from the group consisting of T, V, and I; and X7 may be present or absent, and if present, X7 is selected from the group consisting of A, V, L, I, P, F, M, and W; and wherein either X1, X2, or both X1 and X2 are present, and wherein the first peptide contains a core sequence according to Formula IA wherein X1 is absent, and the second peptide contains a core sequence according to Formula IA wherein X1 and X2 are present.

11. A method of stimulating, increasing, or enhancing nitric oxide production by, or phosphorylation of ERK1/2 and/or eNOS in endothelial cells, which comprises administering to the endothelial cells one or more peptides consisting of 8-35 amino acid residues and having a core sequence represented by Formula IA as follows:

C-X1-X2-C-X3-X4-X5-X6-T-X7-G (SEQ ID NO: 11) (IA)

wherein

X1 may be present or absent, and if present, X1 is selected from the group consisting of A, V, L, I, P, F, M, and W;

X2 may be present or absent, and if present, X2 is selected from the group consisting of D, E, G, N, Q, S, T, Y, and C;

X3 is selected from the group consisting of K, R, and H;

X4 is selected from the group consisting of D, E, K, R, H, Y, F, and W;

X5 is selected from the group consisting of G, N, Q, S, T, Y, and C;

X6 may be present or absent and if present, X6 is selected from the group consisting of T, V, and I; and X7 may be present or absent, and if present, X7 is selected from the group consisting of A, V, L, I, P, F, M, and W; and wherein either X1, X2, or both X1 and X2 are present.

12. A method of treating, inhibiting, or reducing an injury to a cardiac tissue or a heart, wherein the injury is caused by superoxides, ischemia/reperfusion, or myocardial infarction, which comprises stimulating, increasing, or enhancing nitric oxide production by endothelial cells in the cardiac tissue or the heart and/or stimulating or inducing phosphorylation of ERK1/2, eNOS, or both in the endothelial cells by administering to the endothelial cells, before, during, and/or after the injury, one or more peptides consisting of 8-35 amino acid residues and having a core sequence represented by Formula IA as follows:

C-X1-X2-C-X3-X4-X5-X6-T-X7-G (SEQ ID NO: 11) (IA)

wherein

X1 may be present or absent, and if present, X1 is selected from the group consisting of A, V, L, I, P, F, M, and W;

X2 may be present or absent, and if present, X2 is selected from the group consisting of D, E, G, N, Q, S, T, Y, and C;

X3 is selected from the group consisting of K, R, and H;

X4 is selected from the group consisting of D, E, K, R, H, Y, F, and W;

X5 is selected from the group consisting of G, N, Q, S, T, Y, and C;

X6 may be present or absent and if present, X6 is selected from the group consisting of T, V, and I; and X7 may be present or absent, and if present, X7 is selected from the group consisting of A, V, L, I, P, F, M, and W; and wherein either X1, X2, or both X1 and X2 are present.

13. The method of claim 12, wherein the injury is caused by myocardial infarction and the administration reduces the infarct size of the heart.

14. The method of claim 12, wherein the injury is an ischemia/reperfusion injury.

15. The method according to claim 14, wherein the infarct size of the heart is decreased or reduced.

16. The method according to claim 15, wherein the therapeutically effective amount is 0.001 to 100 mg/kg of the subject.

17. The method according to claim 14, wherein the therapeutically effective amount is 0.001 to 100 mg/kg of the subject.

* * * * *

SEQUENCE LISTING

```
<160> NUMBER OF SEQ ID NOS: 12

<210> SEQ ID NO 1
<211> LENGTH: 54
<212> TYPE: PRT
<213> ORGANISM: Homo sapiens
```

<400> SEQUENCE: 1

```
Cys Lys Cys Asn Gly His Ala Ala Arg Cys Val Arg Asp Arg Asp Asp
1               5                   10                  15

Ser Leu Val Cys Asp Cys Arg His Asn Thr Ala Gly Pro Glu Cys Asp
            20                  25                  30

Arg Cys Lys Pro Phe His Tyr Asp Arg Pro Trp Gln Arg Ala Thr Ala
        35                  40                  45

Arg Glu Ala Asn Glu Cys
    50
```

<210> SEQ ID NO 2
<211> LENGTH: 61
<212> TYPE: PRT
<213> ORGANISM: Homo sapiens

<400> SEQUENCE: 2

```
Cys Asn Cys Asn Leu His Ala Arg Arg Cys Arg Phe Asn Met Glu Leu
1               5                   10                  15

Tyr Lys Leu Ser Gly Arg Lys Ser Gly Gly Val Cys Leu Asn Cys Arg
            20                  25                  30

His Asn Thr Ala Gly Arg His Cys His Tyr Cys Lys Glu Gly Tyr Tyr
        35                  40                  45

Arg Asp Met Gly Lys Pro Ile Thr His Arg Lys Ala Cys
    50                  55                  60
```

<210> SEQ ID NO 3
<211> LENGTH: 48
<212> TYPE: PRT
<213> ORGANISM: Homo sapiens

<400> SEQUENCE: 3

```
Cys Asp Cys His Pro Val Gly Ala Ala Gly Lys Thr Cys Asn Gln Thr
1               5                   10                  15

Thr Gly Gln Cys Pro Cys Lys Asp Gly Val Thr Gly Ile Thr Cys Asn
            20                  25                  30

Arg Cys Ala Lys Gly Tyr Gln Gln Ser Arg Ser Pro Ile Ala Pro Cys
        35                  40                  45
```

<210> SEQ ID NO 4
<211> LENGTH: 9
<212> TYPE: PRT
<213> ORGANISM: Homo sapiens

<400> SEQUENCE: 4

```
Cys Asp Cys Arg His Asn Thr Ala Gly
1               5
```

<210> SEQ ID NO 5
<211> LENGTH: 10
<212> TYPE: PRT
<213> ORGANISM: Homo sapiens

<400> SEQUENCE: 5

```
Cys Leu Asn Cys Arg His Asn Thr Ala Gly
1               5                   10
```

<210> SEQ ID NO 6
<211> LENGTH: 11
<212> TYPE: PRT
<213> ORGANISM: Homo sapiens

-continued

<400> SEQUENCE: 6

Cys Pro Cys Lys Asp Gly Val Thr Gly Ile Thr
1 5 10

<210> SEQ ID NO 7
<211> LENGTH: 36
<212> TYPE: PRT
<213> ORGANISM: Homo sapiens

<400> SEQUENCE: 7

Asn Leu His Ala Arg Arg Cys Arg Phe Asn Met Glu Leu Tyr Lys Leu
1 5 10 15

Ser Gly Arg Lys Ser Gly Gly Val Cys Leu Asn Cys Arg His Asn Thr
20 25 30

Ala Gly Arg His
35

<210> SEQ ID NO 8
<211> LENGTH: 27
<212> TYPE: PRT
<213> ORGANISM: Homo sapiens

<400> SEQUENCE: 8

His Pro Val Gly Ala Ala Gly Lys Thr Cys Asn Gln Thr Thr Gly Gln
1 5 10 15

Cys Pro Cys Lys Asp Gly Val Thr Gly Ile Thr
20 25

<210> SEQ ID NO 9
<211> LENGTH: 16
<212> TYPE: PRT
<213> ORGANISM: Homo sapiens

<400> SEQUENCE: 9

His Pro Val Gly Ala Ala Gly Lys Thr Cys Asn Gln Thr Thr Gly Gln
1 5 10 15

<210> SEQ ID NO 10
<211> LENGTH: 11
<212> TYPE: PRT
<213> ORGANISM: Artificial Sequence
<220> FEATURE:
<223> OTHER INFORMATION: Based on human netrin-1
<220> FEATURE:
<221> NAME/KEY: MISC_FEATURE
<222> LOCATION: (2)..(2)
<223> OTHER INFORMATION: Wherein Xaa is present or absent and if present, Xaa is any amino acid residue
<220> FEATURE:
<221> NAME/KEY: MISC_FEATURE
<222> LOCATION: (3)..(3)
<223> OTHER INFORMATION: Wherein Xaa is present or absent and if present, Xaa is any amino acid residue
<220> FEATURE:
<221> NAME/KEY: MISC_FEATURE
<222> LOCATION: (5)..(5)
<223> OTHER INFORMATION: Wherein Xaa is any amino acid residue
<220> FEATURE:
<221> NAME/KEY: MISC_FEATURE
<222> LOCATION: (6)..(6)
<223> OTHER INFORMATION: Wherein Xaa is any amino acid residue
<220> FEATURE:
<221> NAME/KEY: MISC_FEATURE
<222> LOCATION: (7)..(7)
<223> OTHER INFORMATION: Wherein Xaa is any amino acid residue
<220> FEATURE:
<221> NAME/KEY: MISC_FEATURE
<222> LOCATION: (8)..(8)

<223> OTHER INFORMATION: Wherein Xaa is present or absent and if present, Xaa is any amino acid residue
<220> FEATURE:
<221> NAME/KEY: MISC_FEATURE
<222> LOCATION: (10)..(10)
<223> OTHER INFORMATION: Wherein Xaa is present or absent and if present, Xaa is any amino acid residue

<400> SEQUENCE: 10

Cys Xaa Xaa Cys Xaa Xaa Xaa Xaa Thr Xaa Gly
1 5 10

<210> SEQ ID NO 11
<211> LENGTH: 11
<212> TYPE: PRT
<213> ORGANISM: Artificial Sequence
<220> FEATURE:
<223> OTHER INFORMATION: Based on human netrin-1
<220> FEATURE:
<221> NAME/KEY: MISC_FEATURE
<222> LOCATION: (2)..(2)
<223> OTHER INFORMATION: Wherein Xaa is present or absent, and if present, Xaa is selected from the group consisting of A, V, L, I, P, F, M, and W, and analogs and isomers thereof
<220> FEATURE:
<221> NAME/KEY: MISC_FEATURE
<222> LOCATION: (3)..(3)
<223> OTHER INFORMATION: Wherein Xaa is present or absent, and if present, Xaa is selected from the group consisting of D, E, G, N, Q, S, T, Y, and C, and analogs and isomers thereof
<220> FEATURE:
<221> NAME/KEY: MISC_FEATURE
<222> LOCATION: (5)..(5)
<223> OTHER INFORMATION: Wherein Xaa is selected from the group consisting of K, R, and H and analogs and isomers thereof
<220> FEATURE:
<221> NAME/KEY: MISC_FEATURE
<222> LOCATION: (6)..(6)
<223> OTHER INFORMATION: Wherein Xaa is selected from the group consisting of D, E, K, R, H, Y, F, and W, and analogs and isomers thereof
<220> FEATURE:
<221> NAME/KEY: MISC_FEATURE
<222> LOCATION: (7)..(7)
<223> OTHER INFORMATION: Wherein Xaa is selected from the group consisting of G, N, Q, S, T, Y, and C, and analogs and isomers thereof
<220> FEATURE:
<221> NAME/KEY: MISC_FEATURE
<222> LOCATION: (8)..(8)
<223> OTHER INFORMATION: Wherein Xaa is present or absent and if present, Xaa is selected from the group consisting of T, V, and I, and analogs and isomers thereof
<220> FEATURE:
<221> NAME/KEY: MISC_FEATURE
<222> LOCATION: (10)..(1)
<223> OTHER INFORMATION: Wherein Xaa is present or absent, and if present, Xaa is selected from the group consisting of A, V, L, I, P, F, M, and W, and analogs and isomers thereof
<220> FEATURE:
<221> NAME/KEY: misc_feature
<222> LOCATION: (10)..(10)
<223> OTHER INFORMATION: Xaa can be any naturally occurring amino acid

<400> SEQUENCE: 11

Cys Xaa Xaa Cys Xaa Xaa Xaa Xaa Thr Xaa Gly
1 5 10

<210> SEQ ID NO 12
<211> LENGTH: 10
<212> TYPE: PRT
<213> ORGANISM: Artificial Sequence
<220> FEATURE:
<223> OTHER INFORMATION: Based on human netrin-1
<220> FEATURE:

-continued

```
<221> NAME/KEY: MISC_FEATURE
<222> LOCATION: (2)..(2)
<223> OTHER INFORMATION: Wherein Xaa is present or absent, and if
      present, Xaa is selected from the group consisting of A, V, L, I,
      P, F, M, and W, and analogs and isomers thereof
<220> FEATURE:
<221> NAME/KEY: MISC_FEATURE
<222> LOCATION: (3)..(3)
<223> OTHER INFORMATION: Wherein Xaa is present or absent, and if
      present, Xaa is selected from the group consisting of D, E, G, N,
      Q, S, T, Y, and C, and analogs and isomers thereof

<400> SEQUENCE: 12

Cys Xaa Xaa Cys Arg His Asn Thr Ala Gly
1               5                   10
```